US012596109B2

(12) United States Patent
Ali et al.

(10) Patent No.: US 12,596,109 B2
(45) Date of Patent: Apr. 7, 2026

(54) METHOD AND SYSTEM FOR CALIBRATING MEASURED VALUES FOR AMBIENT AIR PARAMETERS USING TRAINED MODELS

(71) Applicant: Ecosystem Informatics Inc., Mississauga (CA)

(72) Inventors: Shirook Ali, Milton (CA); Mohamed Bakr, Ancaster (CA); Houssam Kanj, Waterloo (CA)

(73) Assignee: ECOSYSTEM INFORMATICS INC., Mississauga (CA)

( * ) Notice: Subject to any disclaimer, the term of this patent is extended or adjusted under 35 U.S.C. 154(b) by 459 days.

(21) Appl. No.: 18/076,833

(22) Filed: Dec. 7, 2022

(65) Prior Publication Data
US 2024/0192185 A1      Jun. 13, 2024

(51) Int. Cl.
    *G01N 33/00*          (2006.01)
(52) U.S. Cl.
    CPC ............................... *G01N 33/0006* (2013.01)
(58) Field of Classification Search
    CPC ................................................ G01N 33/0006
    See application file for complete search history.

(56) References Cited

U.S. PATENT DOCUMENTS

| | | |
|---|---|---|
| 7,166,674 B2 | 1/2007 | Datta et al. |
| 9,291,608 B2 | 3/2016 | Herzl et al. |
| 10,277,258 B2 | 4/2019 | Akamine et al. |
| 10,605,633 B2 | 3/2020 | Masson et al. |
| 10,948,471 B1 | 3/2021 | MacMullin et al. |
| 10,956,854 B2 | 3/2021 | Souder et al. |

| | | |
|---|---|---|
| 10,993,647 B2 | 5/2021 | Kale et al. |
| 11,008,853 B2 | 5/2021 | Jones et al. |
| 11,071,887 B2 | 7/2021 | Katis et al. |

(Continued)

FOREIGN PATENT DOCUMENTS

| | | |
|---|---|---|
| AU | 2020100700 | 6/2020 |
| CA | 3214847 | 10/2022 |

(Continued)

OTHER PUBLICATIONS

Machine translation of WO2023135337A1 (Year: 2023).*
Diederik P. Kingma, Jimma Ba "Adam: A Method for Stochastic Optimization", ICLR 2015.
Darvishi Hossein et al., "Sensor-Fault Detection, Isolation and Accommodation for Digital Twins via Modular Data-Driven Architecture", IEEE Sensors Journal, IEEE, USA, vol. 21 No. 4, Oct. 7, 2020, pp. 4827-4838, (12 pages).

(Continued)

*Primary Examiner* — Lee E Rodak
*Assistant Examiner* — Sangkyung Lee

(57)                ABSTRACT

Embodiments described herein generally relate to a method and system for calibrating measured values for ambient air parameters using trained models. In at least one embodiment, the method includes calibrating measured values for an ambient parameter (AP) by generating training dataset points, each of the training dataset point comprising: (i) a first measured value of an AP, generated by a first sensor, at a time instance, and (ii) a second, time-paired measured value for the AP, generated by at least one reference sensor, at the time instance, wherein the first and second values are measured in a localized area surrounding the at least one reference sensor; training an AP-specific calibration model using the training dataset points to generate a trained AP-specific calibration model; applying the trained AP-specific calibration model to a new measured value of the AP, generated by a second sensor.

18 Claims, 13 Drawing Sheets

(56)          References Cited

U.S. PATENT DOCUMENTS

| | | | | |
|---|---|---|---|---|
| 12,380,330 | B1 | 8/2025 | Ali et al. | |
| 2015/0242605 | A1 | 8/2015 | Du et al. | |
| 2019/0176862 | A1* | 6/2019 | Kumar | B61L 25/025 |
| 2020/0126669 | A1* | 4/2020 | Nuernberg | G16H 50/30 |
| 2020/0272944 | A1* | 8/2020 | Goodsitt | G06F 18/214 |
| 2020/0301487 | A1 | 9/2020 | Bamba et al. | |
| 2020/0380378 | A1* | 12/2020 | Moharrer | G06N 20/20 |
| 2021/0003461 | A1 | 1/2021 | Tarkoma et al. | |
| 2022/0333940 | A1 | 10/2022 | Ali et al. | |

FOREIGN PATENT DOCUMENTS

| | | | | |
|---|---|---|---|---|
| CN | 106529081 | 3/2017 | | |
| CN | 112485319 | 1/2023 | | |
| WO | 2019126707 | 6/2019 | | |
| WO | 2022217332 | 10/2022 | | |
| WO | 2022217342 | 10/2022 | | |
| WO | WO-2023135337 A1 * | 7/2023 | | G01D 18/008 |

OTHER PUBLICATIONS

Extended European Search Report received for European Application No. 22787186.0, mailed on Jan. 21, 2025 (8 pages).

When Should a Machine Learning Model Be Retrained? Henrik Skogstrom, dated Nov. 30, 2020 (8 pages).

AI at your fingertips—Make any security camera smarter for less than $50 using Tensorflow, Armindo Cachada, dated Aug. 13, 2018 (17 pages).

Office Action dated Jul. 10, 2025, U.S. Appl. No. 17/718,804 (42 pages).

Multivariate Time Series Forecasting with LSTMs in Keras, Jason Brownlee, dated Oct. 21, 2020, available at https://machinelearningmastery.com/multivariate-time-series-forecasting-lstms-keras/ (12 pages).

Neural Network Retraining for Model Serving, Diego Klabjan et al., Dated Apr. 29, 2020 (4 pages).

* cited by examiner

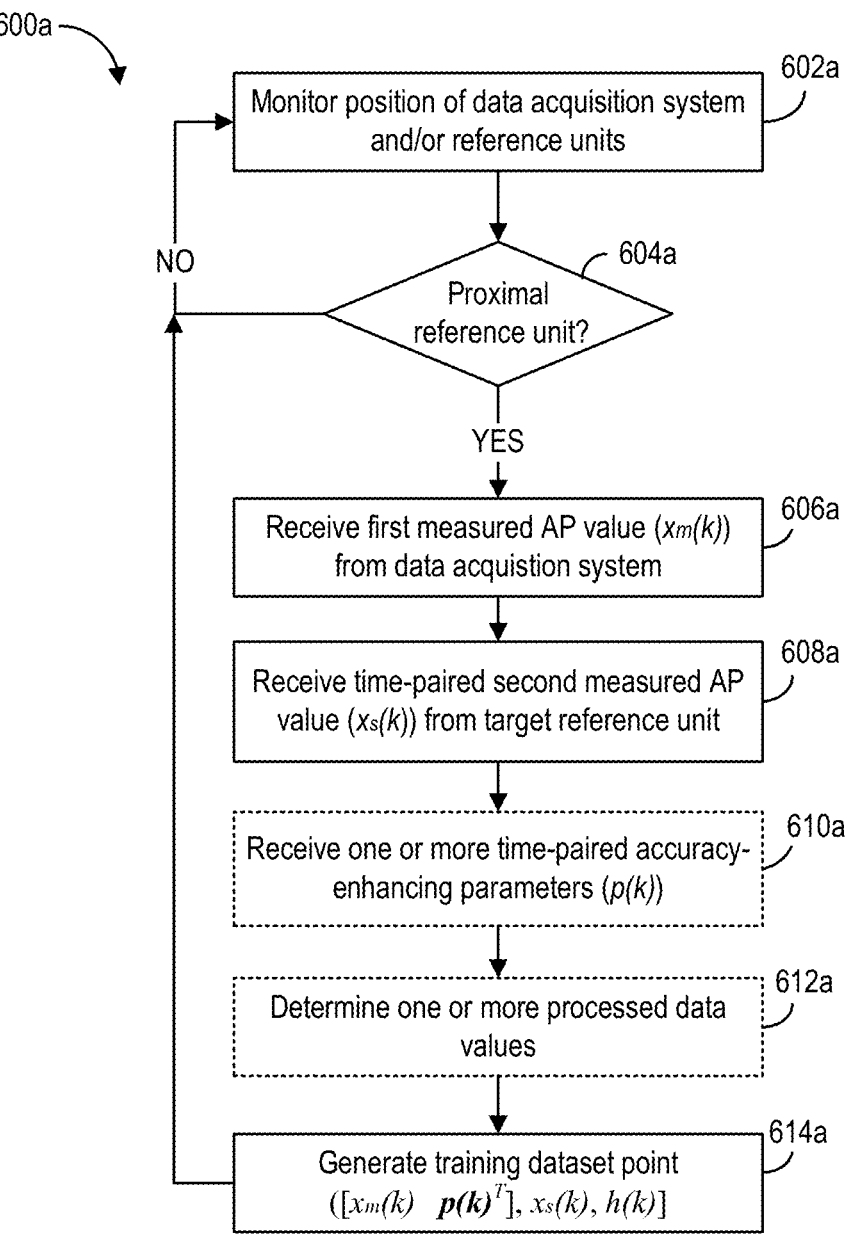

600a

Monitor position of data acquisition system
and/or reference units — 602a

Proximal
reference unit? — 604a

NO

YES

Receive first measured AP value ($x_m(k)$)
from data acquistion system — 606a

Receive time-paired second measured AP
value ($x_s(k)$) from target reference unit — 608a Receive one or more time-paired accuracy-
enhancing parameters ($p(k)$) — 610a Determine one or more processed data
values — 612a Generate training dataset point
($[x_m(k) \quad p(k)^T], x_s(k), h(k)$) — 614a

FIG. 6A

METHOD AND SYSTEM FOR CALIBRATING MEASURED VALUES FOR AMBIENT AIR PARAMETERS USING TRAINED MODELS

FIELD

The disclosed embodiments generally relate to monitoring of ambient air parameters, and in particular, to a method and system for calibrating measured values for ambient air parameters using trained models, including trained machine learning models.

BACKGROUND

Ambient air parameters, such as the concentration of gaseous air pollutants and air temperature, may be monitored for a variety of reasons, such as alerting populations of health risks, evaluating compliance with air quality standards, and mapping air quality patterns. There remains a need in the art for accurate, economical, and efficient monitoring of ambient parameters, particularly using sensors mounted on mobile platforms.

SUMMARY

In at least one broad aspect, there is provided a method for calibrating measured values for an ambient parameter (AP), comprising: generating, using at least one processor, one or more training dataset points, each of the one or more training dataset point comprising: (i) a first measured value of an AP, generated by a first sensor, at a time instance, and (ii) a second, time-paired measured value for the AP, generated by at least one reference sensor, at the time instance, wherein the first and second values are measured in a localized area surrounding the at least one reference sensor; training, using the at least one processor, an AP-specific calibration model using the one or more training dataset points to generate a trained AP-specific calibration model; applying the trained AP-specific calibration model to a new measured value of the AP, generated by a second sensor; and based on the applying, outputting a corresponding output calibrated measured value of the AP.

In at least one embodiment, the method is performed on a server computer, and the at least one processor comprises a server processor.

In at least one embodiment, the method further comprising, for each of the one or more training dataset points, initially: receiving the first measured value of the AP from the first sensor; and receiving the second measured value from the at least one reference sensor.

In at least one embodiment, the trained calibration model is a trained machine learning model.

In at least one embodiment, the trained machine learning model is a trained artificial neural network (ANN).

In at least one embodiment, for each of the one or more training dataset points, prior to the generating that training dataset points, the method further comprises: monitoring a location of the first sensor; based on the monitoring, determining that the first sensor is within a threshold distance of the at least one reference sensor; and if the first sensor is within the threshold distance, generating the training dataset point.

In at least one embodiment, the first sensor and the second sensor are part of a sensor subsystem of a mobile or stationary data acquisition system, wherein the mobile data acquisition system is mounted to a mobile platform.

In at least one embodiment, the at least one reference sensor is part of at least one stationary or mobile reference sensor unit.

In at least one embodiment, each of the one or more training dataset points further comprises a positive scale factor, and generating each of the one or more training dataset points comprises: determining a distance between the first sensor and the reference sensor at the time instance; and determining the positive scale factor based on the distance, wherein the determination is made based on a pre-defined positive scale factor function.

In at least one embodiment, each of the one or more training dataset points further comprises one or more accuracy-enhancing parameters generated at the time instance.

In at least one embodiment, the second sensor is the same or different from the first sensor.

In another broad aspect, there is provided a system for calibrating measured values for an ambient parameter (AP), the system comprising: a first and second sensor for monitoring an AP; at least one reference sensors for monitoring the AP in a corresponding localized area surrounding the corresponding reference sensor; and a server comprising a server memory coupled to at least one server processor, wherein the at least one server processor is configured for: generating one or more training dataset points, each of the one or more training dataset point comprising: (i) a first measured value of the AP, generated by the first sensor, at a time instance, and (ii) a second, time-paired measured value for the AP, generated by at least one, of the at least one reference sensors, at the time instance, wherein the first and second values are measured in the localized area corresponding to the at least one reference sensor; training an AP-specific calibration model using the one or more training dataset points to generate a trained calibration model; applying the trained calibration model to a new measured value of the AP, generated by the second sensor; and based on the applying, outputting a corresponding calibrated measured value of the AP.

In at least one embodiment, the at least one server processor is further configured for: for each of the one or more training dataset points, initially: receiving the first measured value of the AP from the first sensor; and receiving the second measured value from the at least one reference sensor.

In at least one embodiment, the trained calibration model is a trained machine learning model.

In at least one embodiment, the trained machine learning model is a trained artificial neural network (ANN).

In at least one embodiment, each of the one or more training dataset points, prior to the generating that training dataset points, wherein the at least one server processor is configured for: monitoring a location of the first sensor; based on the monitoring, determining that the first sensor is within a threshold distance of the at least one reference sensor; and if the first sensor is within the threshold distance, generating the training dataset point.

In at least one embodiment, the first sensor and the second sensor are part of a sensor subsystem of a mobile or stationary data acquisition system, wherein the mobile data acquisition system is mounted to a mobile platform.

In at least one embodiment, the at least one reference sensor is part of at least one stationary or mobile reference sensor unit.

In at least one embodiment, each of the one or more training dataset points further comprises a positive scale factor, and generating each of the one or more training dataset points comprises: determining a distance between the first sensor and the reference sensor at the time instance; and determining the positive scale factor based on the distance, wherein the determination is made based on a pre-defined positive scale factor function.

In at least one embodiment, each of the one or more training dataset points further comprises one or more accuracy-enhancing parameters generated at the time instance.

In different embodiments, the present invention may comprise a method or system comprising any combination of elements or features described herein, or which specifically omits any particular feature or element described herein.

BRIEF DESCRIPTION OF THE DRAWINGS

In the drawings, like elements may be assigned like reference numerals. The drawings are not necessarily to scale, with the emphasis instead placed upon the principles of the present disclosure. Additionally, each of the embodiments depicted are but one of a number of possible arrangements utilizing the fundamental concepts of the present disclosure.

FIG. 6A is a process flow for an example method for generating training dataset points, which can be used for training a calibration model.

DETAILED DESCRIPTION OF THE EMBODIMENTS

Figure 1:
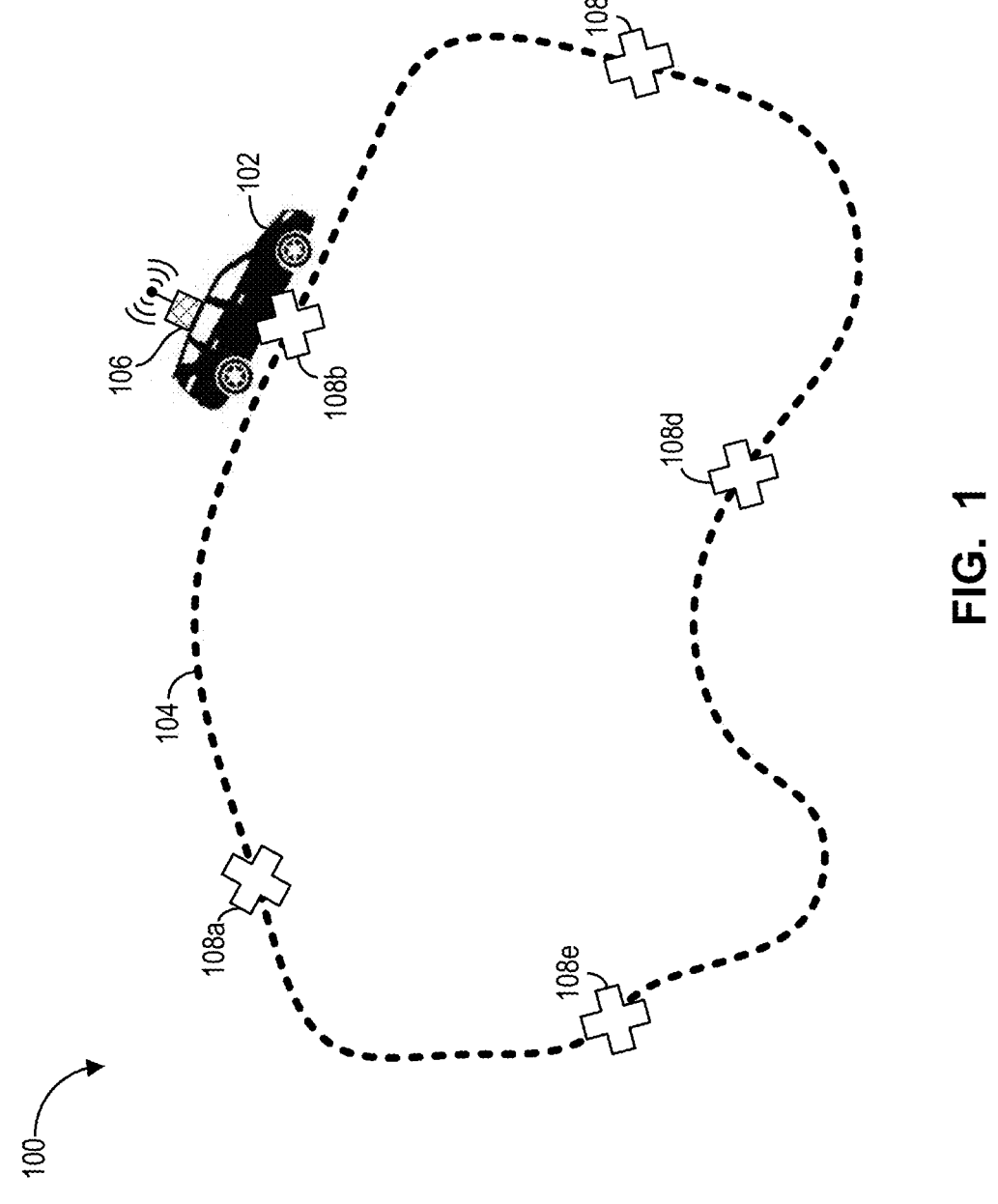
FIG. 1 is an illustration of a mobile platform, equipped with a mobile data acquisition system, moving along a data collection route.

Embodiments herein generally relate to monitoring air quality and/or atmospheric condition.

I. Definitions

Any term or expression not expressly defined herein shall have its commonly accepted definition understood by a person skilled in the art. As used herein, the following terms have the following meanings.

"Ambient parameter" or "AP" refers to any physically measurable property of air. In embodiments, the AP may be a concentration of a gaseous component of air with non-limiting examples of such gaseous components being carbon monoxide (CO), carbon dioxide ($CO_2$), nitrous oxide (NO), nitrogen oxides of the formula $NO_x$ such as nitrogen dioxide ($NO_2$), ozone ($O_3$), methane ($CH_4$), and sulfur oxides of the formula $SO_x$ such as sulfur dioxide ($SO_2$). In other embodiments, the AP may be a concentration of suspended particulate matter (PM) in general, or a concentration of suspended particulate matter of a specific composition such as lead. In still other non-limiting embodiments, the AP may be a weather condition, such as air temperature, humidity, barometric pressure, and wind speed.

"AP-specific calibration model", "AP calibration model" or "calibration model", refers to one or more rules (e.g., expressed by mathematical formulae, and/or logical relationships), stored in a memory, that receives an input value, comprising a measured and un-calibrated AP value, and determines an output comprising an estimated or predicted value for a corresponding calibrated AP value. The calibration model may therefore compensate for a calibration offset affecting the measured AP value.

"GPS module" refers to a device that includes an antenna for receiving satellite navigation signals (e.g., signals transmitted by the Global Positioning System (GPS), the Global Navigation Satellite System (GLONASS), the Galileo positioning system, the Beidou Navigation Satellite System, or satellite navigation systems), and an operatively connected processor that is configured with a set of instructions stored on a memory, to analyze such signals to determine the location of the module, and optionally, other kinematic information such as distance travelled, direction of movement, speed, and acceleration of the module. GPS modules are known in the art, and do not, by themselves constitute the present invention. Persons skilled in the art may refer to a satellite navigation signal receiver module as a "GPS receiver," or a "GNSS receiver," depending on the type of satellite navigation signal used by the module.

"Memory" refers to a non-transitory tangible computer-readable medium for storing information in a format readable by a processor, and/or instructions readable by a processor to implement an algorithm. The term "memory" includes a plurality of physically discrete, operatively connected devices despite use of the term in the singular. Non-limiting types of memory include solid-state, optical, and magnetic computer readable media. Memory may be non-volatile or volatile. Instructions stored by a memory may be based on a plurality of programming languages known in the art, with non-limiting examples including the C, C++, Python™, MATLAB™, and Java™ programming languages.

"Mobile platform" refers to any device, or object, which is not necessarily limited to a fixed stationary geolocation and/or is otherwise able to move between geolocations. Mobile platforms may include any consumer or industrial means of transportation, such as automobiles, trucks, buses, trains, tractors, motorcycles, or bicycles, whether powered or not. Mobile platforms may further include handheld or portable devices or objects which are manually moved, such as by a pedestrian. For example, these can include handheld phones, but can also include backpacks, suitcases, and the like.

"Reference sensor unit" refers to any device unit that includes one or more sensors. In some examples, the one or more sensors may measure different ambient parameters (APs). For instance, each sensor—in the reference unit—can measure a single, corresponding AP. The sensors can be scientific-grade sensors, which generate highly accurate sensor readings. Each reference sensor unit can also include other hardware, such as hardware for stabilizing and/or calibrating sensor data (e.g., vibration platforms, temperature and humidity control systems, etc.). A reference sensor unit can be stationary in a fixed geographic location and/or mobile. If the reference sensor unit is mobile, it can be mounted to, or integrated within (e.g., partially or fully integrated), a mobile platform.

"Processor" refers to one or more electronic devices that is/are capable of reading and executing instructions stored on a memory to perform operations on data, which may be stored on a memory or provided in a data signal. The term "processor" includes a plurality of physically discrete, operatively connected devices despite use of the term in the singular. Non-limiting examples of processors include devices referred to as microprocessors, microcontrollers, central processing units (CPU), and digital signal processors.

"Training", refers to a process, implemented by a processor according to an algorithm stored in a memory, that determines the value(s) of one or more variable(s) of the rule(s) defining a calibration model, based on a training dataset of known values of an ambient parameter generated by both a mobile and stationary sensor (as well as, in some examples, known values of other accuracy-enhancing parameters) in order to calibrate, and increase the accuracy of the value of the ambient parameter as measured by the mobile sensor.

II. General Overview

As stated in the background, ambient air parameters, such as the concentration of gaseous air pollutants and air temperature, may be monitored for a variety of reasons using various sensors. While the monitoring sensors may be stationary or mobile, a mobile sensor can monitor air quality over a greater geographic area than would be possible if the sensor were stationary.

In more detail, FIG. 1 illustrates a mobile platform (102) moving along a data collection route (104). Data collection route (104) may define a path through an indoor and/or outdoor environment (100). For ease of description, mobile platform (102) is exemplified as a vehicle (102). However, the mobile platform (102) may comprise any other object capable of moving between one or more geolocations, as previously defined.

A data acquisition system (106)—or DAS (106), for short—is mounted to the vehicle (102). DAS (106) can include one or more sensors for measuring various ambient parameters (AP) (e.g., CO, particulate matter (PM), $CO_2$, NO, $SO_2$ concentrations). As used herein, sensors in the data acquisition system (106) may be referenced as "data acquisition system (DAS) sensors", which generate respective DAS sensor data.

As the vehicle (102) traverses the data collection route (104), the DAS sensors measure one or more respective ambient parameters (APs). For example, the DAS sensors may generate sensor data indicative of CO concentration at each of several different geographic locations (108a)-(108e), along route (104). To that end, each DAS sensor can generate corresponding sensor data, for a corresponding monitored AP.

Once the sensor data is collected, the sensor data may be processed for use in a wide variety of applications. For example, the DAS sensor data can be used for determining air quality patterns in the environment (100). In some examples, the system generates a report which includes the determined air quality patterns.

While the DAS sensors offer a unique advantage in enabling monitoring over a greater geographic area, these sensors also suffer from distinct drawbacks. For example, changing vehicle motion results in temperature, wind direction, and wind speed variations, which can affect the accuracy of the DAS sensor readings. This, in turn, has practical implications for the cost, efficiency, and reliability of monitoring performed on a large mobility scale. Some of these factors also affect sensor readings, even when the data acquisition system (DAS) is fixed or stationary. For example, temperature and humidity factors can still affect the accuracy of fixed or stationary sensor readings.

Notably, these error-inducing factors are problematic where it is desirable for the DAS to generate high accuracy sensor readings. In many cases, generating highly-accurate sensor readings requires large, bulky and expensive data acquisition systems. These systems encapsulate expensive, high profile, scientific-grade sensors, as well as additionally, heavy and sophisticated hardware for stabilizing and calibrating sensor readings to compensate for the various error-inducing factors, e.g., as noted above. The hardware can include, for example, temperature and humidity control systems, and the like. For mobile data acquisition systems, the hardware can additionally include large and sophisticated anti-vibration platforms for the sensors. In some cases, the hardware requires customization to accommodate specific use applications.

Accordingly, owing to their bulky, heavy weight and expensive nature—it can be difficult to deploy these data acquisition systems (DAS) in a highly scalable manner, i.e., to achieve wide geographic monitoring of ambient parameters.

For example, the costly nature of these systems makes it prohibitive to deploy many of these systems around many fixed or mobile positions. Additionally, the large size and heavy weight also makes it difficult for laypersons to easily mount, or deploy many the systems around many fixed or mobile positions. In many cases, it is necessary for experienced technicians to be present to securely mount the heavy DAS enclosures to fixed or mobile platforms. More generally, the bulky size of these systems makes them visually unappealing when mounted to platforms.

In view of the foregoing, described embodiments provide for a method and system for calibrating inaccurate measured ambient parameter (AP) values using machine learning models.

As described, embodiments herein allow generating more accurate measurements of AP values without necessitating high grade and/or expensive sensors. Rather, high accuracy is achievable using only low-cost, and low profile sensors. In turn, this reduces the overall cost of the data acquisition system.

As well, described embodiments do not necessitate use of expensive and heavy-weight ancillary hardware (e.g., stabilizing or calibrating hardware for sensors) to generate accurate sensor readings. This, as well, reduces the overall cost of the system, and also enables encapsulating the system in a light-weight and small form factor enclosure. This light weight and small form factor enclosure is more easily deployed, by laypersons, to both fixed and mobile platforms.

More broadly, owing to the low cost, light weight and small form factor nature of the described data acquisition systems (DASs)—it is possible to deploy the DASs in a highly-scalable manner and achieve wider and more accurate geographic monitoring of ambient parameters.

As explained, to achieve the aforementioned—the disclosed embodiments employ a calibration model for calibrating the inaccurate measured AP values from the data acquisition system (DAS) sensors. The calibration model may be, for example, a trained machine learning model, such as a trained artificial neural network (ANN). In more detail, the trained calibration model adjusts, or compensates, for calibration offsets affecting AP values measured using the DAS sensors.

The calibration model may be applied in real-time, or near real-time. Accordingly, the trained model receives un-calibrated AP values as they are generated by the data acquisition system (DAS) sensors, and returns—instantaneously, or near instantaneously (e.g., real-time or near real-time)—corresponding calibrated AP values.

In some examples, the calibration model is trained and/or hosted on the "cloud" (e.g., remote servers). In other examples, the calibration model is trained and/or hosted locally, e.g., on the data acquisition system (DAS) or any other system or device.

The use of a machine learning model offers a convenient alternative and/or supplement, to using costly scientific-grade sensors, and/or otherwise, expensive large and heavy-weight stabilization/calibration hardware for sensors.

More generally, the trained machine learning model can receive less accurate sensor readings from low-cost, low profile sensors. In turn, the trained model can provide accuracy correction, and output sensor readings with analo-gous accuracy to the high-grade sensors that are stabilized, or calibrated, using expensive hardware.

III. Example System

Figure 2:
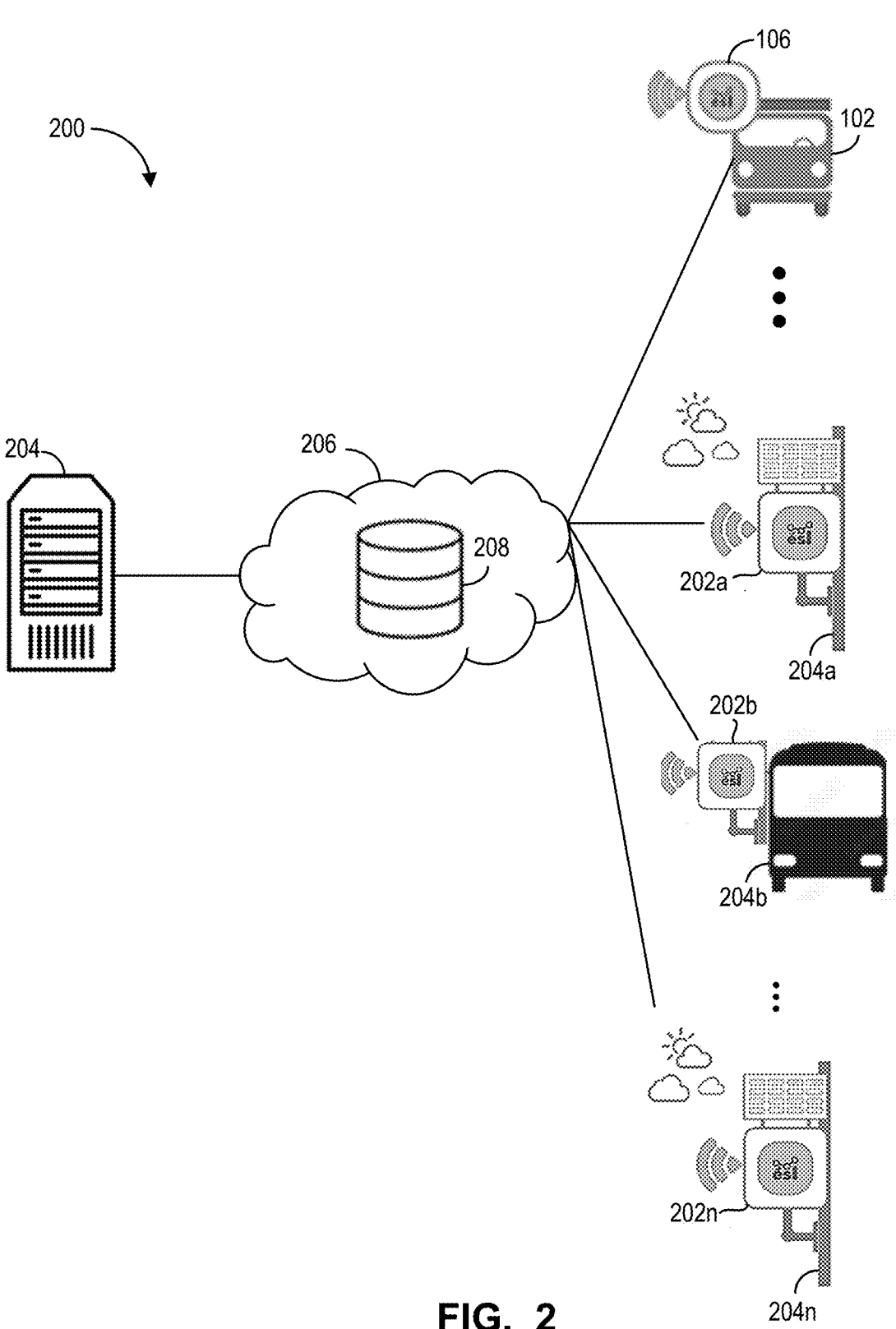
FIG. 2 is a simplified block diagram of a system for automated calibration of measured ambient air parameter values.

Reference is now made to FIG. 2, which shows a sim-plified block diagram for a system (200) for training an ambient parameter (AP) calibration model. Concurrent ref-erence is also made to FIGS. 3A-3D, which schematically illustrate example environments (300a)-(300d) for training the calibration model.

As best shown in FIG. 2, the system (200) generally includes the data acquisition system (106), and one or more reference sensor units (202a)-(202n).

(i.) Example Data Acquisition System

Data acquisition system (106) can include one or more sensors for measuring various ambient parameters (APs). While only a single acquisition system (106) is illustrated, any number of acquisition systems (106) can be included in system (200).

Figure 3A:
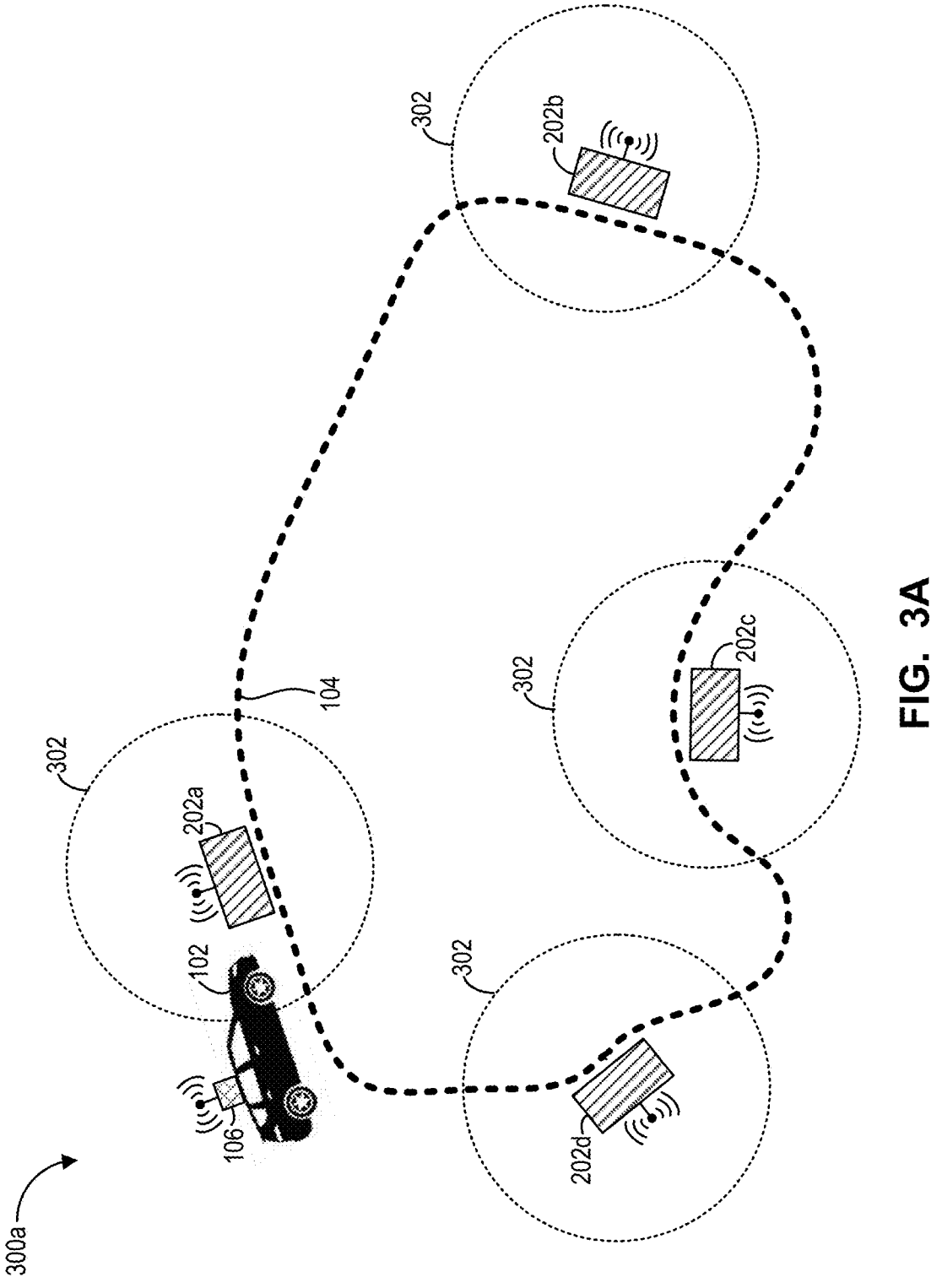
FIG. 3A is analogous to the illustration in FIG. 1, but further illustrates one or more stationary reference sensor units located on, or proximal, the data collection route.
Figure 3B:
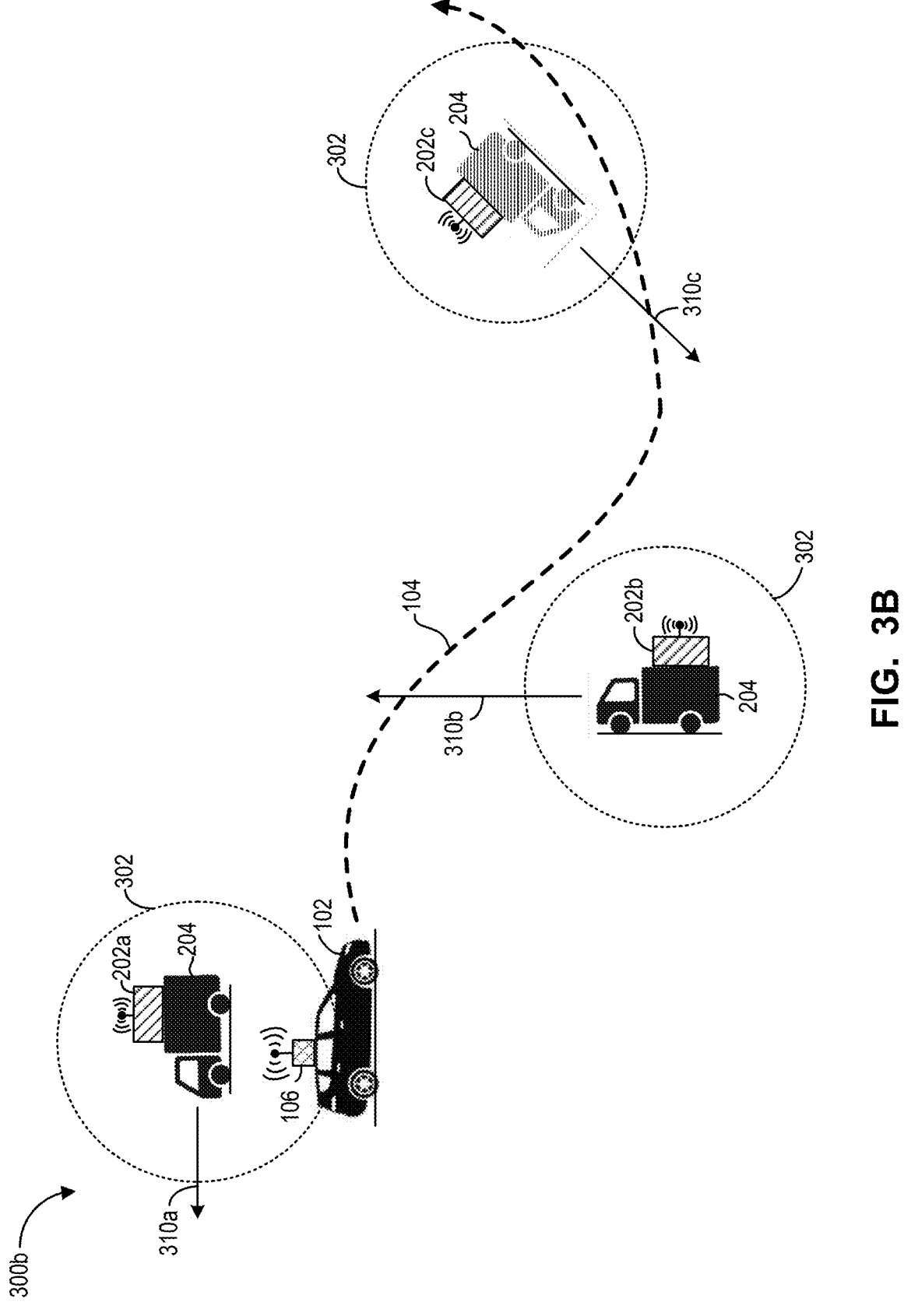
FIG. 3B illustrates one or more mobile reference sensor units located on, or proximal, the data collection route.
Figure 3C:
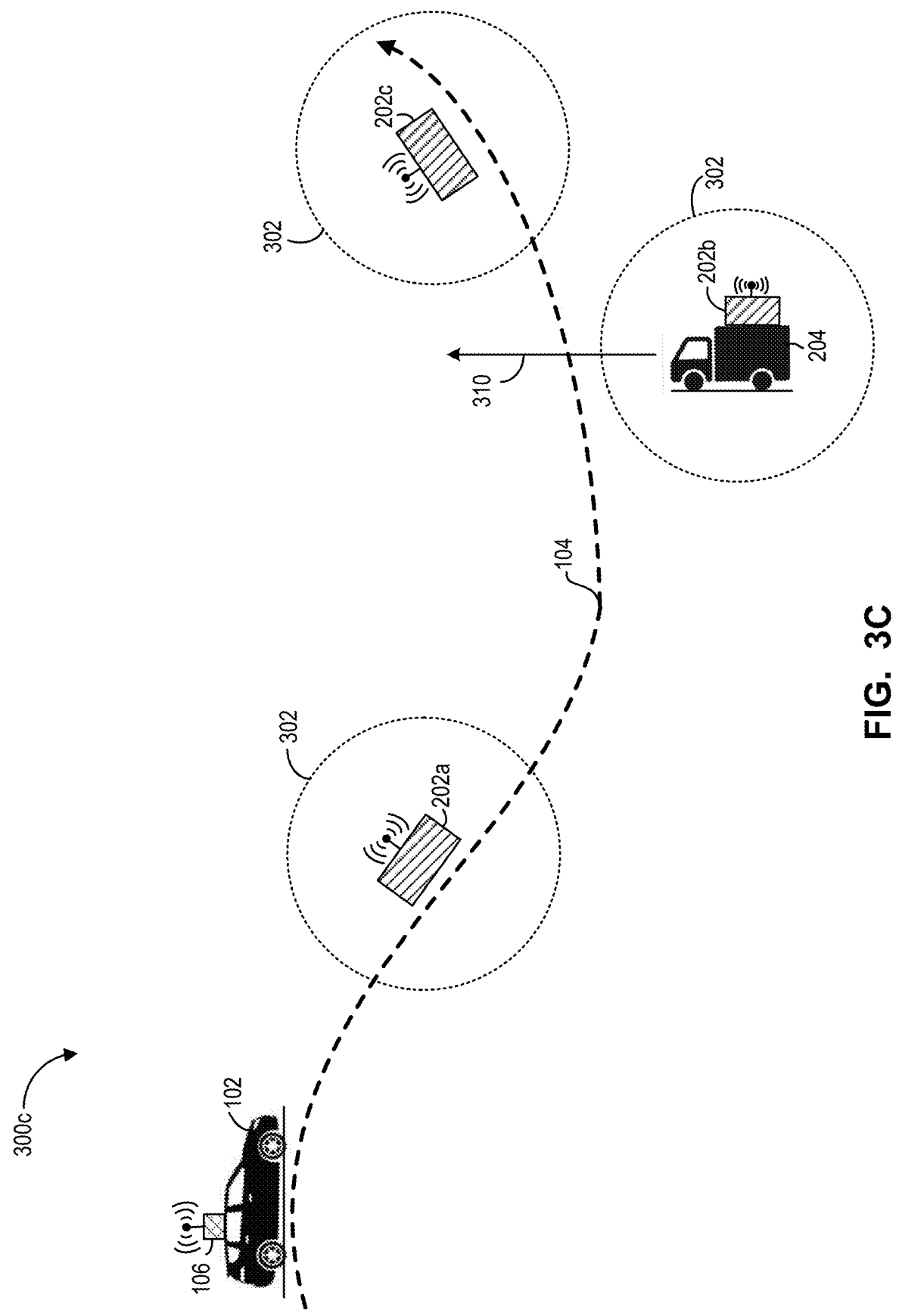
FIG. 3C illustrates a combination of stationary and mobile reference sensor units located on, or proximal, the data collection route.

The data acquisition system (106) can be mobile and/or stationary. For instance, the data acquisition system (106) can be a mobile system (FIG. 1), and moves to different positions along a data collection route (104) (FIGS. 3A-3C). Accordingly, the sensors measure various ambient param-eters (APs), at different geographic positions along the data collection route (104).

To that end, while FIGS. 1 and 3A illustrate the data collection route (104) as a closed loop where the vehicle returns to its start point, the data collection route (104) is not so-limited. In other words, the data collection route (104) may have any desired route or path configuration, including any open and/or closed configuration. For example, FIGS. 3B and 3C exemplify an "open" data collection route (104).

Where the data acquisition system (106) is mobile—the system (106) is mounted to a mobile platform (102), such as a vehicle. In these examples, the system (106) is physically separated from the mobile platform (102).

In other examples, the mobile system (106) is not neces-sarily separated from the mobile platform (102), but is fully or partially integrated within the mobile platform (102). For example, the mobile system (106) can comprise an elec-tronic hardware portion of a vehicle's on-board computing system.

Figure 3D:
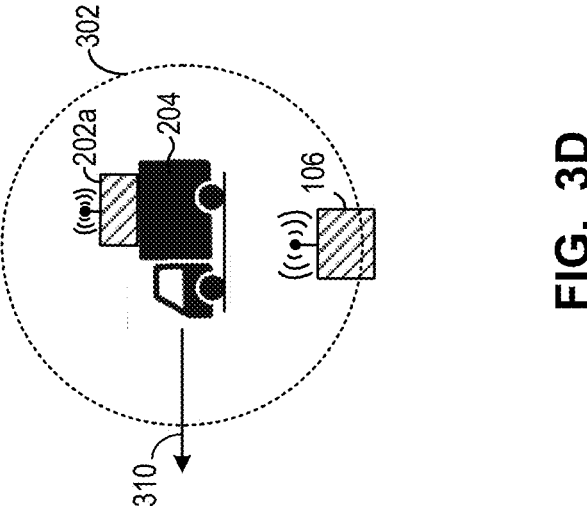
FIG. 3D illustrates a stationary data acquisition system, and a mobile reference sensor unit.

In other examples, the data acquisition system (106) is stationary (FIG. 3D). In turn, the sensors measure APs at only a single geographic location. It is possible that the same data acquisition system (106) is mobile at times, and sta-tionary at other times.

(ii.) Example Reference Sensor Units

Referring still to FIG. 2, system (200) also includes one or more reference sensor units (202a)-(202n).

Each reference unit (202) can include one or more sensors (also referenced herein as "reference sensors"). The refer-ence sensors are designed to measure values for various ambient parameters (APs) in air samples localized around the respective reference unit (202). As used herein, sensor data generated by reference sensors may be referenced herein as "reference sensor data", i.e., as distinguished from data acquisition system (DAS) sensor data.

More generally, in the described systems—the reference units (202) are a source of more accurate sensor data, and in some examples, more accurate than the sensors included in the data acquisition system (106). The reference units (202) can include, for instance, expensive high-grade sensors that generate scientifically-accurate sensor readings. Reference units (202) can also include hardware used for stabilization and/or calibration of sensor data. In some examples, the reference units (202) are fixed or mobile government envi-ronmental stations.

As provided below, the more-accurate sensor data—generated by the reference units (202)—is used to train a calibration model. The calibration model, in turn, is deployed to correct the less-accurate sensor data, from the data acquisition system (106).

As best shown in FIGS. 3A-3D, similar to the data acquisition system (106)—the reference units (202) may either be stationary or mobile.

As exemplified in FIG. 3A, the reference units (202) can be stationary, and positioned at different geographic loca-tions on, or near, data collection route (104) of the mobile system (106). For example, each stationary unit (202) can be mountable, of affixed, to various stationary structures (204a)-(204n) along route (104) (e.g., a street lighting pole, or a building) (see e.g., FIG. 2).

As exemplified in FIGS. 3B and 3D, the reference units (202) can also be mobile. For example, the reference units (202) can be mounted to various mobile platforms (e.g., vehicles, busses, suitcases, etc.).

In these examples, each reference unit (202) can follow a corresponding reference motion trajectory (310) (e.g., 310a-310c in FIG. 3B). The reference trajectory (310) can define a specific time-scheduled route through the surrounding geographic area.

The reference trajectory (310) can be pre-defined or can be generated on the spot. If the reference unit (202) is mounted to an automated mobile object (e.g., a self-driving vehicle), the automated object can automatically move the reference unit (202) along the desired reference trajectory.

In some examples (FIG. 3C), the environment can include a mix of both mobile and stationary reference sensor units.

To that end, the reference unit (202) can be separate from the stationary or mobile platform, or can be integrated (e.g., fully or partially) into the stationary or mobile platform.

(iii.) Example Computer Server and Communication Network

Referring still to FIG. 2, the data acquisition system (106) and reference units (202) may be coupled to a computer server (204), via a communication network (206).

Communication network (206) can be an internet, or intranet network. In some examples, network (206) may be connected to the internet. Typically, the connection between network (206) and the internet may be made via a firewall server (not shown). In some cases, there may be multiple links or firewalls, or both, between network (206) and the Internet. Some organizations may operate multiple networks (206) or virtual networks (206), which can be internet-worked or isolated. These have been omitted for ease of illustration, however it will be understood that the teachings herein can be applied to such systems. Network (206) may be constructed from one or more computer network technologies, such as IEEE 802.3 (Ethernet), IEEE 802.11 and similar technologies.

Server computer (204) may be in a server-client relationship with each data acquisition system (106) and the one or more reference units (202a)-(202n).

In some examples, using communication network (206), computer server (204) can access (e.g., receive and/or request) sensor data generated by sensors located in each of the data acquisition system (DAS) (106) and the reference units (202), e.g., as represented by the connecting lines in FIG. 2.

To that end, various data communications methods are employable to transmit sensor data, from each of the DAS (106) and the reference sensor units (202), to server (204).

For example, the DAS (106) and/or reference units (202) may wirelessly transmits sensor data, via the communications network (206), to a memory of a cloud database (208), which stores the sensor data so that it can be accessed subsequently by server computer (204).

In other examples, the DAS (106) and/or reference units (202) may directly transmit some, or all, of the sensor data via the communications network (206) to a memory that is local to server computer (204).

In still other examples, the computer server (204) may be physically connected to the DAS (106) and/or reference units (202), and further, the DAS system (106) and/or reference units (202) may store some or all of the sensor data to a memory that is local in the respective system or unit, so that it may be processed by a processor that is local to the system or unit, in an "offline mode" without the need for a communications network.

As explained herein, computer server (204)—and/or cloud server (208)—can host an untrained calibration model. The untrained calibration model is then trained, on server (204, 208), using training datasets in order to generate the trained calibration model. Once trained, the calibration model can remain hosted on the computer server (204, 208). For example, the trained calibration model is stored on a server memory, and is applied to new measured AP values from the DAS (106) (or any other DAS (106)).

In other cases, once the calibrations model is trained, the calibration model is transmitted to external computing systems. For example, the trained calibration model is transmitted back to the DAS (106), any other DAS (106), and/or the reference units (202).

If hosted on the DAS (106), the calibrations model is applied directly by the DAS (106) to newly generated DAS sensor data.

If hosted on the reference units (202), the units can receive un-calibrated APs from a DAS (106), and apply the model to generate calibrated APs. These calibrated APs can be transmitted back to the same DAS (106), another DAS (106), the server (204, 208), or otherwise, any other system or device.

IV. Overlap Time Segments (Thin Time-Slice Segments)

Irrespective of whether the DAS (106) and/or reference units (202) are stationary or mobile—in FIGS. 3A-3D, there are time segments of overlap (e.g., geographic overlap) between the data acquisition system (106) and the reference units (202). These overlap time segments are also known herein as "thin time-slice segments".

To further clarify this concept, reference is made to FIGS. 3A-3D. In FIGS. 3A-3D, the thin time-slice segments generally occur when data acquisition system (DAS) (106) is within a pre-defined distance or proximity of a reference unit (202).

In some examples, a geographic boundary region (302) is defined around each reference unit (202). Accordingly, a thin time-slice segment occurs in the time period when the DAS (106) is geographically within the boundary region (302).

The boundary region (302) can be, for example, within 0 to 50 meters around the reference unit (202). While illustrated as a circle, the boundary region (302) can have any other shape or configuration. Further, different types of boundary regions (302) can be defined around different reference units (202).

In some examples, the size (or area) of the boundary region (302) varies based on the apparent or determined level of pollution in the surrounding area. For example, if the area is more polluted, this can require higher resolution measurements—therefore a smaller boundary region is used. The significance of relying on a smaller boundary region will be explained shortly.

In FIG. 3A, the thin time slice-segments occur when the mobile DAS (106) passes within the boundary region (302) of the fixed reference units (202).

In FIG. 3B, the thin time-slice segments occur when the mobile DAS (106) passes within the boundary region (302) of one of the mobile reference units (202). In other words, the thin time-slice segments occur when the DAS' data collection route (104) generally intersects with the reference trajectory (310) for a reference unit (202).

In FIG. 3D, the thin time-slice segments occur when the mobile reference unit (202) passes in proximity of the stationary DAS (106). In other words, the reference trajectory (310)—for the reference unit (202)—generally intersects the geographic location of the stationary DAS (106). In this manner, the DAS (106) is intermittently located within the boundary region (302).

In FIG. 3C, the thin time-slice segments occur in both cases where either the mobile DAS (106) passes by a stationary reference unit (202a), or otherwise, intersects the trajectory of a mobile reference unit (202b).

In an ideal case, for a given measured AP (e.g., CO concentration)—the value of the AP reading from the reference sensor (202) should be substantially identical to the readings generated by the data acquisition system (DAS) sensors, during the overlap time segments (i.e., thin time-slice segments). This is because, during these time segments, both the reference and data acquisition sensors are measuring the same AP in the same air sample (e.g., within boundary region (302)).

More practically, however, the data acquisition system (DAS) sensor readings deviate from the reference sensor readings. This is owing to calibration errors affecting the data acquisition system (DAS) sensors, but not otherwise affecting the reference sensors, at least to the same degree, as discussed above.

For this reason, in described embodiments—the thin time-slice segments are used to train one or more ambient parameter (AP) calibration models. As described below, during the thin time-slice segments, the calibration model(s) are trained to determine the offset difference between: (i) the more-accurate data from the reference sensors; and (ii) the less-accurate data from the data acquisition system sensors, within the same air sample (e.g., boundary (302)).

V. Ambient Parameter (AP) Calibration Model

As noted above, the reference sensor data—generated by the reference sensor units (202)—is used to train an ambient parameter (AP) calibration model, during the thin time-slice segments.

As also noted, the AP calibration model can be hosted on a "cloud" server and/or locally, e.g., on the data acquisition system (106) or on the reference unit (202).

More broadly, a calibration model is gradually trained by comparing: (i) the less-accurate sensor data from the data acquisition system (DAS) (106), to (ii) the more-accurate reference sensor data, during the overlap time segments (i.e., the thin-time slice segments). The thin time-slice segments are used for training, as these are the time segments when the DAS and reference sensors should have identical sensors readings.

In some examples, the calibration model is also trained using other accuracy-enhancing input features, that can also affect the calibration offset. For example, as discussed below, this can include accounting for temperature, humidity, wind-speed factors, among other factors.

Once trained, the calibration model can receive an un-calibrated, lower-accuracy AP value, measured by a sensor of the same (or different) data acquisition system (106). In turn, the calibration model outputs a corresponding pre-dicted more-accurate calibrated AP value. The trained calibration model can also receive the one or more accuracy-enhancing parameters, to enhance predictive output.

Accordingly, the calibration model enables reliable use of sensors in the data acquisition system (106) (e.g., low-profile, less expensive sensors) for environmental monitoring. The calibration model also does not rely on expensive, heavy-duty hardware, conventionally required for stabilizing or calibrating sensor readings.

In at least one example, the system can generate different calibration models for different types of measurable ambient parameters (APs). Accordingly, the system can generate multiple "AP-specific" calibration models.

For example, the system can generate a first AP calibration model for correcting CO readings, a second AP calibration model for correcting $CO_2$ readings, a third AP calibration model for correcting NO readings, and so on.

To that end, each of the data acquisition system (106), and one or more of the reference units (202), can include sensors for monitoring more than one type of AP (e.g., CO, $CO_2$, NO, etc.), which are then used to train the one or more AP-specific calibration model. Each AP-specific calibration model is then applied to calibrate a corresponding measured AP value. In other examples, different DASs (106) are used for training different AP models, e.g., different DASs are equipped with different sensors.

In other examples, a single AP calibration model is trained to correct for multiple types of AP (e.g., two or more). In this example, the model is trained with respective training data for multiple APs.

VI. Positive Scale Factor

In at least some examples, a positive scale factor (h(k)) is used during training of the ambient parameter (AP) calibration model. The positive scale factor is used to place more emphasis on training values generated when the DAS (106) is more proximal to the reference units (202).

Figure 7:
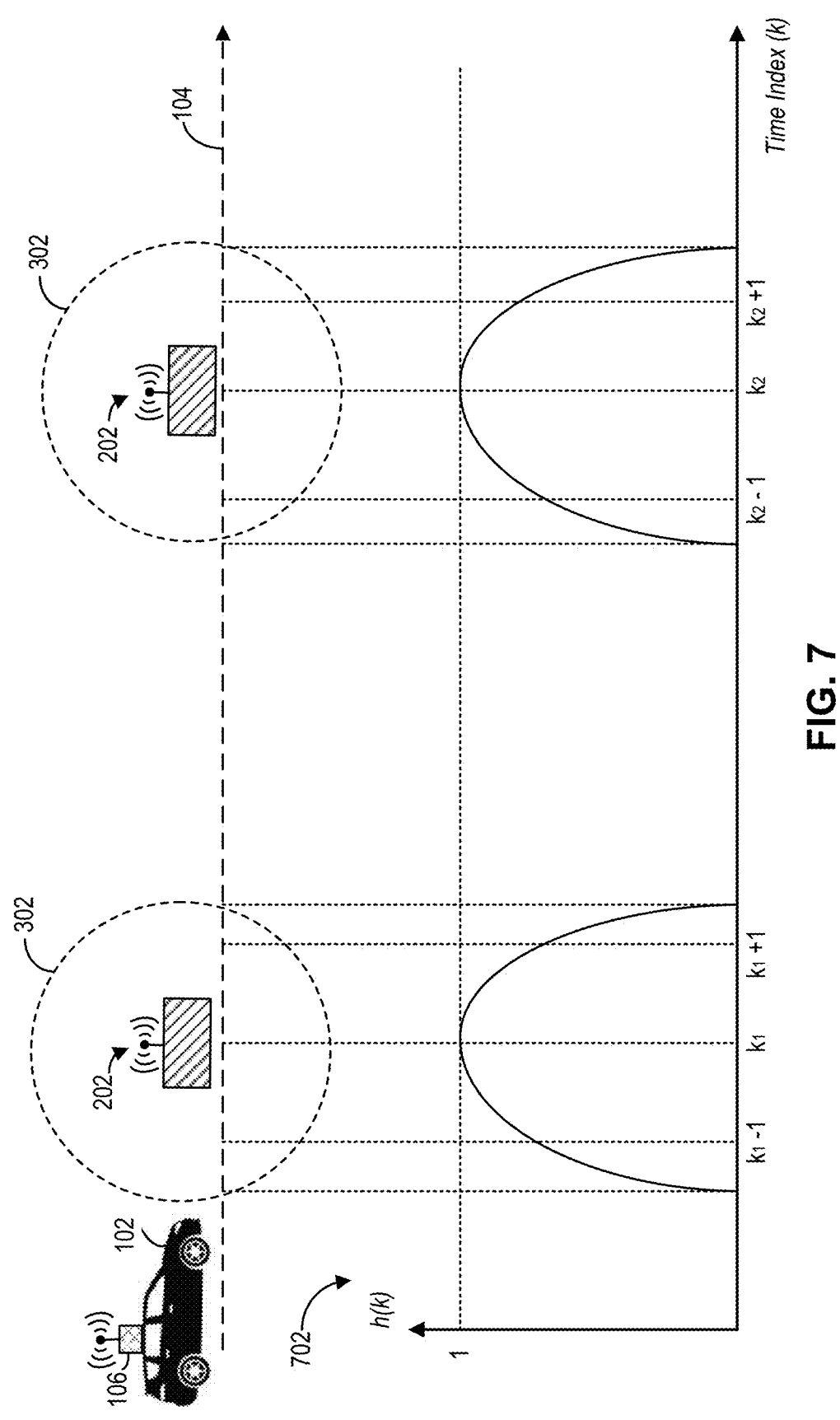
FIG. 7 is a schematic illustration of a function for determining positive scale factors for use in training a calibration model.

To further clarify this concept, reference is briefly made to FIG. 7. FIG. 7 illustrates two stationary reference units (202) spaced along the data collection route (104). The boundary region (302) is demarcated around each stationary reference unit (202).

As shown in plot (702), a positive scale factor (h(k)) (otherwise referred to herein as a "trust weight") varies as a function of proximity of the data acquisition system (DAS) (106) to a stationary reference unit (202).

For example, when the mobile DAS (106) is outside the boundary region (302), the positive scale factor is "0". This is because the mobile and stationary sensors are not monitoring the same air sample, and therefore, training values generated by the sensors—at this position—are of minimal relevance for training the calibration model.

In contrast, within the boundary region (302), the positive scale factor (h(k)) increases until the mobile system (106) is in the same position as the stationary reference unit (202). At this point, the measured training AP values, from the mobile system (106) and stationary unit (202), is of greatest relevance for training the calibration model. This is because the mobile system (106) and the stationary unit (202) are monitoring AP in a near identical air sample. Accordingly, the readings from these two systems should be expected to be near-identical.

A similar concept is applied in other examples, where the reference sensor unit (202) is mobile, and the data acquisition system (106) is either stationary or mobile.

In some examples, the scale factor (h(k)) is related to distance—between the DAS (106) and a given reference unit (202)—by a scale factor function. The scale factor function can decrease (e.g., monotonically decrease), with increased distance between the reference unit (202) and the DAS (106). In some cases, the scale factor function varies in a range between [0,1].

For example, the scale factor function can dictate that: (i) outside of a boundary region (302), the scale factor (h(k)) is zero; and (ii) within the boundary region (302), the scale factor increases (e.g., monotonically increases) as a function of more proximal distance to reference unit (202).

Within the boundary region (302) the scale factor function can also comprise any suitable function, including a linear or non-linear function. The function can decrease (e.g., mono-tonically decrease) as a function of distance between DAS (106) and reference unit (202). For instance, as exemplified in FIG. 7, the function is a non-linear parabolic-like function.

In at least one example, a different scale factor function is defined for each reference unit (202). For instance, for different reference units (202)—a different scale factor function is defined within the boundary region (302). For example, a first linear function may be defined for reference unit (202a), while a second non-linear function may be defined for reference unit (202b). Accordingly, a unit-specific scale factor function can be stored in association with each unit, e.g., stored on the server memory.

In some examples, the scale factor function can also be binary. For example, (i) outside of a boundary region (302), the scale factor (h(k)) is zero; and (ii) within the boundary region (302), the scale factor is one.

VII. Deployment of Reference Sensors During Training and Application of Calibration Model(s)

In at least one embodiment, the reference sensor units (202) are only deployed during training of the calibration model. In other words, once the calibration model is trained—the reference sensor units (202) are removed from the environment, or their use otherwise neglected (e.g., as shown in FIG. 1). In this sense, the pictorial illustration in FIGS. 3A-3D exemplifies a model "training" mode, while FIG. 1 exemplifies a model "application" or "inference" mode for the system.

In other examples, the training process is iterative. In other words, the system can continue to train the calibration model(s) to enhance their predictive output. In these cases, some or all of reference sensor units (202) are not removed, even during the inference-phase of the calibration model (e.g., during application of the calibration model).

In these examples, during the inference-phase—the reference units (202), however, can be relocated to different positions along the data collection route (104)—or new sensors added—to generate a greater diversity of training datasets during the iterative training. Further, mobile reference units (202) can be moved along different reference trajectories (310).

In FIGS. 3A-3D, the arrangement, movement and positioning, of the reference sensor units (202) can define a reference sensor unit configuration.

Any reference sensor configuration can be employed for calibration model training. For example, the configuration can include any number of fixed reference sensor units (202) located at any number of geographic locations around the route (104). Further, the configuration can include any number of mobile reference sensor units (202), moving along any corresponding route trajectory (310). The reference sensor configuration can include reference sensor units (202) with the same, or different reference sensors for measuring any number of APs.

In at least one example, the reference sensor unit configuration is selected with a view to the desired model training. For example, fixed reference sensors are positioned around geographic points where certain types of training data can be collected. For example, if it is desired to generate more training datasets in humid or windy conditions, more stationary sensor reference units (202) are added to areas along data collection route (104) which are more humid or windy. This allows training the system to more effectively calibrate measured AP values. By a similar token, mobile reference sensors (202) can be moved along any desired route where certain types of desired training datasets can be collected.

In some cases, different reference sensor configurations can be used with different AP-specific models.

VIII. Example Methods

The following is a description of various example methods for operating the systems and devices described herein.

(i.) Example Method for Generating Training Datasets for Training an Ambient Parameter (AP) Calibration Model Reference is now made to FIG. 6A, which shows a process flow for an example method (600a) for generating training datasets (e.g., 504b in FIG. 5), which are used for training a calibration model (e.g., 504a in FIG. 5).

In the illustrated example, method (600a) is performed using processor (502) of computer server (204) (e.g., a cloud server). However, in other embodiments, the method (600a) is performed locally, e.g., on the data acquisition system (106).

At a high level, and as explained previously—training values are received at the server (204), during the overlap time segments (i.e., thin time-slice segments), between the data acquisition system (106) and the reference units (202), in FIGS. 3A-3D.

More generally, when the data acquisition system (106) is proximal to a reference unit (202) (e.g., within the boundary region (302))—the server (204) receives sensor data generated by each of the data acquisition system (106) and the corresponding reference sensor unit (202).

For example, in FIG. 3B, the server (204) receives sensor data from the data acquisition system (DAS) (106) and the reference sensor unit (202a). The sensor data can be in respect of a single ambient parameter (AP), or multiple APs.

The received DAS and reference sensor data express a measured value for one or more APs, in the common air sample surrounding each of the data acquisition system (DAS) (106) and reference sensor unit (202), e.g., within boundary region (302) during a thin time-slice segment.

As noted earlier, it is expected that during the thin time-slice segments, the measured AP values—generated by the DAS sensor(s)—will deviate from those generated from the reference sensors, due to calibration offsets affecting the DAS.

As the reference sensor data is assumed more accurate than the DAS sensor data, the calibration model is trained using AP values measured by the reference sensors during the thin time-slice segments.

During training, the AP values from the reference sensors define the target, or expected, output of the trained calibration model. In this manner, once trained, the calibration model receives an un-calibrated input AP value, generated by the DAS sensors. The calibrated model is then configured to output a calibrated AP value, which is substantially similar to the expected/target AP value measured by the more accurate reference sensors.

Now in more detail, referring still to FIG. 6A—at act (602a), the server (204) monitors the location of the data acquisition system (106) and/or the reference units (202).

The purpose of the monitoring is to determine whether the data acquisition system (DAS) (106) is within a threshold proximity to a reference unit (202). For example, this involves determining if the DAS (106) is within the boundary region (302) associated with a reference unit (202).

At act (604a), the server (204) can determine if the data acquisition system (106) is within threshold proximity of a reference unit (202) (e.g., within the boundary region (302)). If this holds true, this may satisfy a condition for generating training dataset points. This condition would correspond to the existence of an overlap time segment (i.e., a thin time-slice segment) between the data acquisition system (106) and reference unit (202). As explained, the thin time-slice segments are ideal time segments for generating training dataset points, to train the calibration model.

To that end, the system can monitor proximity of the DAS (106) to a reference unit (202) in various manners.

In at least one example, the monitoring is based on location data generated, and received, from one or more of the DAS (106) and the reference units (202).

For instance, with respect to a mobile DAS (106) (FIGS. 3A-3C)—the DAS (106) can generate location data using one or more of the GPS module (412) and/or a telematics systems of a vehicle (102). The location data is transmitted from DAS (106) to the server (204), automatically or upon request.

Further, with respect to the reference units (202)—in at least one example, the server (204) can store pre-determined geographic locations of each stationary reference unit (202) (FIG. 3A). In other cases, the server (204) can also store a pre-determined route trajectory (104) for each mobile reference unit (202) (FIG. 3B). In some examples, the trajectory information includes, not only the geographic route path, but also the time schedule when the mobile reference unit (202) is expected to pass by different locations along the path (104). This pre-determined information is stored on the server memory (504).

Accordingly, at act (604a), upon receiving location data from the mobile DAS (106) (FIGS. 3A-3C), the server (204) can cross-reference the mobile system's current location to the pre-determined locations or route trajectory of each reference unit (202). Accordingly, if the mobile system's (106) location is within a pre-determined distance of a stationary or mobile reference unit (202), the system can determine the beginning (or existence) of an overlap time segment at act (604a), wherein training dataset points can be generated.

In other examples, in FIG. 3A, server (204) may not necessarily store pre-determined locations or route trajectories of each reference unit (202). Rather, each reference unit (202) may independently communicate its own geographic location and/or route trajectory to the server (204). For example, each reference unit (202) may connect to a location sensor (e.g., GPS modules), which generates respective location data. The location data is transmitted automatically, or upon request, to the server (204). The location data is stored in association with each reference unit (202), and used to determine the position of each reference unit (202) relative to the mobile system (106).

Continuing with reference to FIG. 6A—at act (604a), if the mobile system (106) is not within proximity of a reference unit (202), then method (600a) can return to act (602a) to continue monitoring. Otherwise, if sufficient proximity is detected, the system can begin generating one or more training dataset points.

Acts (606a)-(614a) clarify an example process for generating a single training dataset point, for a single ambient parameter (AP) type (e.g., CO concentration). However, a similar process can be used to generate different training dataset points, for other AP types, i.e., to train other AP-specific calibration models.

At act (606a), server (204) receives a first measured AP value from the data acquisition system (DAS) (106), which is located proximal a reference unit (202). The first measured value can relate to a target ambient parameter (AP), around which a calibration model is built. For example, this can be a measured value for CO concentration within the boundary region 302 (FIG. 3), and at a given time index (k).

The measured AP value is acquired via DAS sensor data, generated by a relevant sensor of the DAS' sensor subsystem (408) (e.g., CO concentration sensor (408d)). The sensor data is generated, and transmitted to server (204) automatically, or otherwise, generated and transmitted upon request by the server (204).

As used herein, the notation $x_m(k)$ expresses the value of a measured AP by the DAS (106), acquired at time $k\Delta t$, wherein $\Delta t$ is the sampling time step of the AP sensor and $k=0, 1, 2$, etc.

At act (608a), the server (204) also receives a second, time-paired measured value for the target AP, but from the target reference sensor unit (202).

The target reference unit (202), in act (606a), is the reference unit determined to be proximal to the DAS (106), i.e., at act (604a). It is assumed that the target reference unit (202) includes sensors capable of measuring the same type of target $\Delta t$ measured by the DAS (106), to provide one-to-one mapping.

As used herein, the notation $x_s(k)$ expresses the value of a measured AP value by the target reference unit (202), acquired at time $k\Delta t$, wherein $\Delta t$ is the sampling time step of the AP sensor in the reference unit (202) and $k=0, 1, 2$, etc.

At act (608a), "time-paired", as used herein, means that the first AP value and the second AP value, are measured at the same time, or substantially the same time, such that the generated first and second AP values can be considered as representing a simultaneous state of the target AP in an air sample, in the vicinity of physically attached DAS and reference sensors (e.g., within boundary region (302)).

In some examples, server (204) can determine, at act (608a), that two AP values are time-paired based on a known sampling rate of the DAS and reference sensors. For example, sensors—of each of the DAS (106) and reference unit (202)—may sample at the same time step rate. Accordingly, server (304) may time-pair sensor values generated at the same "k-th" step.

In other examples, the sensor data—generated by each of the DAS and reference unit—may be timestamped. The timestamping is generated using a synchronized internal clock of each of the mobile system and the target reference unit. Accordingly, the server (204) can time-pair measured AP values associated with the same timestamp.

As explained earlier, in an ideal case, $x_m(k)$ is identical to the time-paired $x_s(k)$. However, these values realistically deviate due to calibration offsets affecting the mobile system (106), but not the stationary unit (202).

While method (600a) illustrates act (606a) being performed prior to act (608a), in other cases, acts (606a) and (608a) are performed concurrently, or partially concurrently.

At act (610a), in some examples, the server (204) additionally receives one or more accuracy-enhancing calibration parameter values, from data acquisition system (106) and/or target reference unit (202).

Accuracy-enhancing parameters can enhance, or otherwise improve, the accuracy of the calibration model. These include various parameters expected to affect the calibration offset in the DAS (106).

To that end, accuracy-enhancing parameters—received at act (610a)—can be time-paired with the received first and second AP values (606a and 608a). That is, the measured values of these parameters are obtained generally at the same time instance as the measured first and second AP values.

Examples of the accuracy-enhancing parameters include various ambient air parameters, obtained from one or more AP sensors (408g)-(408f), of the DAS' sensor subsystem (408) and/or reference unit (202). For instance, temperature data, humidity data, pressure data and wind speed data, generated by the relevant sensors, may enhance the accuracy of trained calibration model.

The accuracy-enhancing parameters can also include the speed of the data acquisition system (106) and/or reference unit (202). For example, faster speeds—using larger discrete time increments—may result in less reliable training data values, and are accordingly, accounted for in training the model. The size of the discrete time increment "k" may also be accounted for, as an accuracy-enhancing parameter.

As explained, the calibration model is trained to detect correlations between these parameters (e.g., temperature, pressure, and wind, GPS location)—at a given time instance—with a relevant calibration offset.

Accuracy-enhancing parameters can also include other ambient gas parameters, generated by one or more other gas sensors. For example, this includes other measured AP values from other AP sensors on a target reference unit (202). For example, if the calibration model is being trained to calibrate CO measurements, the other AP measurements can include NO or $CO_2$ measurements from the reference sensors.

In still yet other examples, accuracy-enhancing parameters can include one or more mobile platform parameters, associated with the DAS (106) and/or reference unit (202). For example, this includes parameter values acquired from the mobile platform data input interface (414), e.g., vehicle speed, vehicle location, and the like.

In some examples, at act (610a), the accuracy-enhancing parameters are amalgamated into a single vector matrix expressed as (p(k)).

At act (612a), in at least one example, the system can generate one or more processed data values.

For instance, this can involve processing training dataset values—received at acts (606a)-(610a), by normalizing these values, filtering the values (e.g., noise removal), or the like. In turn, one or more corresponding processed training values are generated.

In at least one embodiment, at act (612a), generating processed data values involves determining a time-paired positive scale factor (h(k)).

As previously described, the positive scale factor (h(k)) is used during training of the calibration model to place more emphasis on training values generated when the data acquisition system (106) is more proximal to the reference units (202).

The positive scale factor (h(k)) can increase, as the data acquisition system (106) is in closer proximity to a reference sensor unit (202). More generally, the positive scale factor (h(k)) can vary according to a pre-defined scale factor function, which relates the value of positive scale factor (h(k)) to distance proximity. As noted before, this functions can be defined in any manner (e.g., a linear or non-linear function).

In some examples, the positive scale factor (h(k)) is zero, when the DAS (106) is outside of a boundary region (302). In some cases, the positive scale factor (h(k)) varies in a range between [0, 1].

Determining the positive scale factor (h(k)) can involve: (i) initially, determining the difference in distance between the DAS (106) and the target reference unit (202) at time-step "k" (e.g., based on known or received location data); (ii) applying the distance to the pre-defined scale factor function, to resolve a value for the positive scale factor (h(k)).

At act (614a), a training dataset point is generated, expressed as ([$x_m$(k)p(k)$^T$],$x_s$(k)], h(k)), wherein $x_m$(k) is the measured AP at the k-th time instance by a DAS sensor of the data acquisition system (106); p(k)$^T$ is a transpose vector of the accuracy-enhancing calibration parameters at the time-paired k-th time instance; and $x_s$(k) is the measured AP value at the time-paired k-th time instance based on reference sensor data generated by the target reference sensor unit (202).

In some examples, each of the variables, in the training dataset point, are not necessarily generated at the same "k" time step, but within a few steps of the "kth" time step (e.g., k±5).

In some examples, the training dataset point may also include the determined scale factor (h(k)), also determined at the time-paired k-th time instance.

In training the calibration model using a supervised learning method-[$x_m$(k) p(k)$^T$] represents the input feature space, whereas $x_s$(k) represents the target output feature. The calibration model is trained to approximate the mapping between the input feature space [$x_m$(k) p(k)$^T$], and the target output feature space $x_s$(k), for the k-th time step.

Further, in some examples, h(k) is used during model training to place more emphasis on minimizing the errors corresponding to the time instances when the DAS (106) is closest to the reference units (202). Accordingly, the input feature space would comprise [$x_m$(k) p(k)$^T$ h(k)].

Continuing with reference to FIG. 6A, subsequent to act (614a), method (600a) can return to act (602a) to continue monitoring the position of the data acquisition system (106) and/or reference units (202).

(ii.) Multiple Iterations of Method (600a) for
Generating Additional Training Dataset Points Method (600a) can iterate as many times as necessary, or desired, to generate any number of training dataset points.

For example, in FIGS. 3A-3C, as the DAS (106) moves along the route (104), method (600a) can iterate at any pre-defined time or frequency interval to generate a corresponding number of training dataset points.

In this case, the multiple generated training dataset points can be said to be "time-separated". "Time-separated", as used herein, means that the plurality of training dataset points are measured at different times (e.g., k, k+1, k+2, k+n, etc.). In some examples, the training dataset points are time separated based on the sampling rate frequency of the mobile and stationery sensors.

To that end, if the data acquisition system (DAS) (106) is still within proximal range of the same reference unit (202), it can continue generating new training dataset points in association with that reference unit (202). Accordingly, during a single overlap time segment (i.e., a thin time-slice segment), it is possible for multiple training dataset points to be generated. However, these multiple training dataset points may be associated with different positive scale factors (h(k)), i.e., depending on where the DAS (106) is located within the boundary region (302) (FIG. 7).

In other cases, the data acquisition system (DAS) (106) may move-on to within proximal range of a new target reference unit (202), and can generate new training dataset points based on the new reference unit (202).

It is also possible for a mobile DAS (106) to repeat its movement along the entirety, or any portion, of the route (104). For example, the mobile system (106) can navigate route (104)—or any portion thereof—at a first time instance. Mobile system (106) can then repeat navigation of route (104), or any portion thereof, at a later time instance. In these example, the mobile system (106) re-passes by one or more of same reference units (202), and generates new training dataset points.

In at least one example, the mobile system (106) is made to repeat its movement along route (104) to accommodate for different ambient conditions. For example, the mobile system (106) is trained along route (104) in different humidity, wind, pressure and temperature conditions. As explained, these ambient conditions are factored into model training as accuracy-enhancing parameters (p(k)). By training in different conditions, a diversified array of training dataset points is generated, which can enhance the accuracy and reliability of the calibration model.

In the example of FIG. 3D, as new mobile reference units (202) pass-by the DAS (106) at different times, new training dataset points are also generated in respect of each new mobile reference unit (202) that passes-by.

(iii.) Example Method for Training and Applying Calibration Model

Figure 6B:
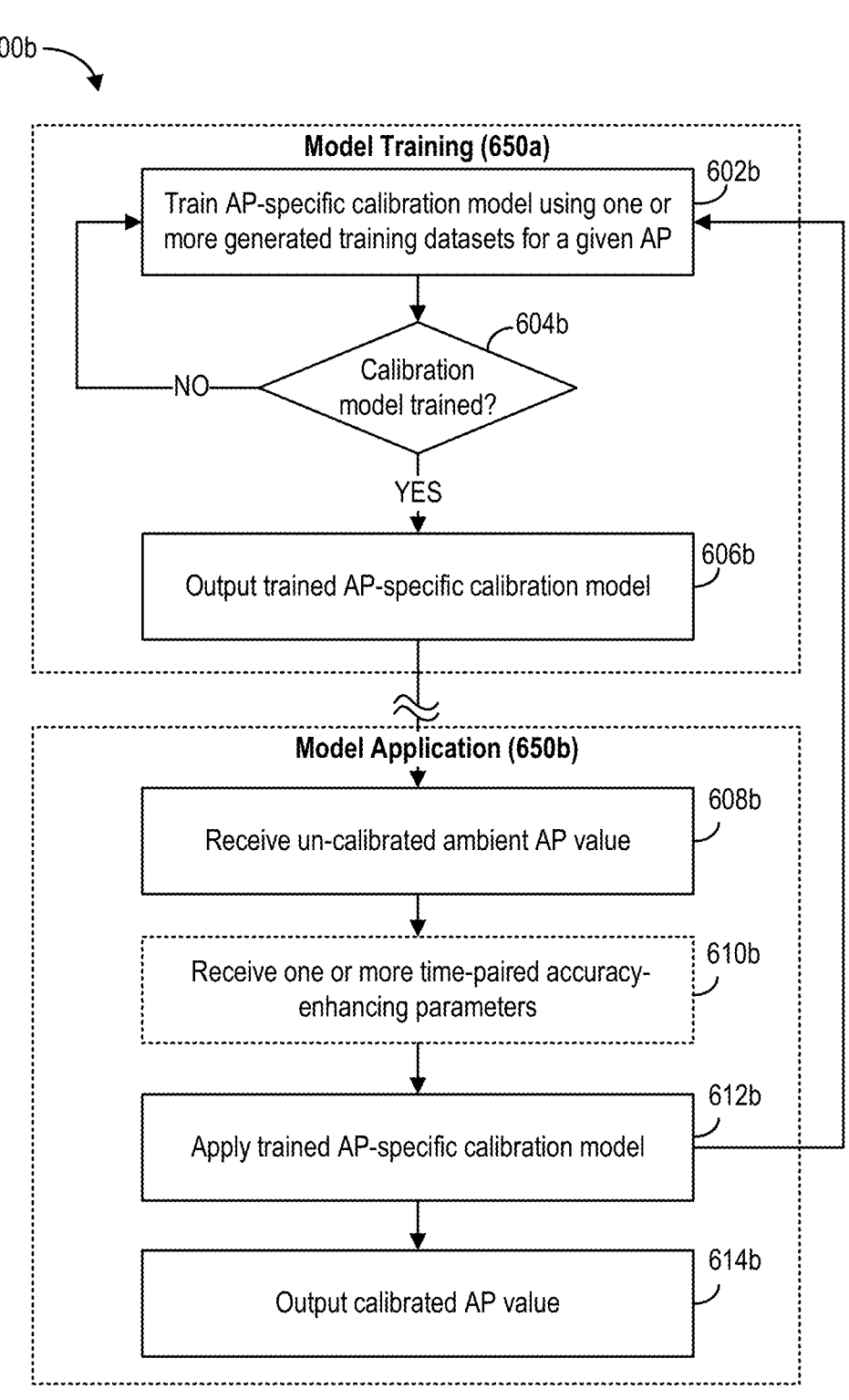
FIG. 6B is a process flow for an example method for training a calibration model, and subsequently applying the trained calibration model.

Reference is now made to FIG. 6B, which shows a process flow for an example method (600*b*) for training a calibration model using training dataset points (e.g., generated in method (600*a*)), and further, applying the trained calibration model to newly measured AP values.

In the exemplified embodiment, method (600*b*) is performed on the processor (502) of server (204). In other examples, method (600*b*) is also performed locally, e.g., on the processor (402) of the data acquisition system (106).

At a broad level, method (600*b*) includes two sub-process flows: (i) initially, training the calibration model (650*a*); and (ii) subsequently, applying the trained calibration model (650*b*).

In some examples, the training is continuously performed, even as the trained model is being applied.

Figure 5:
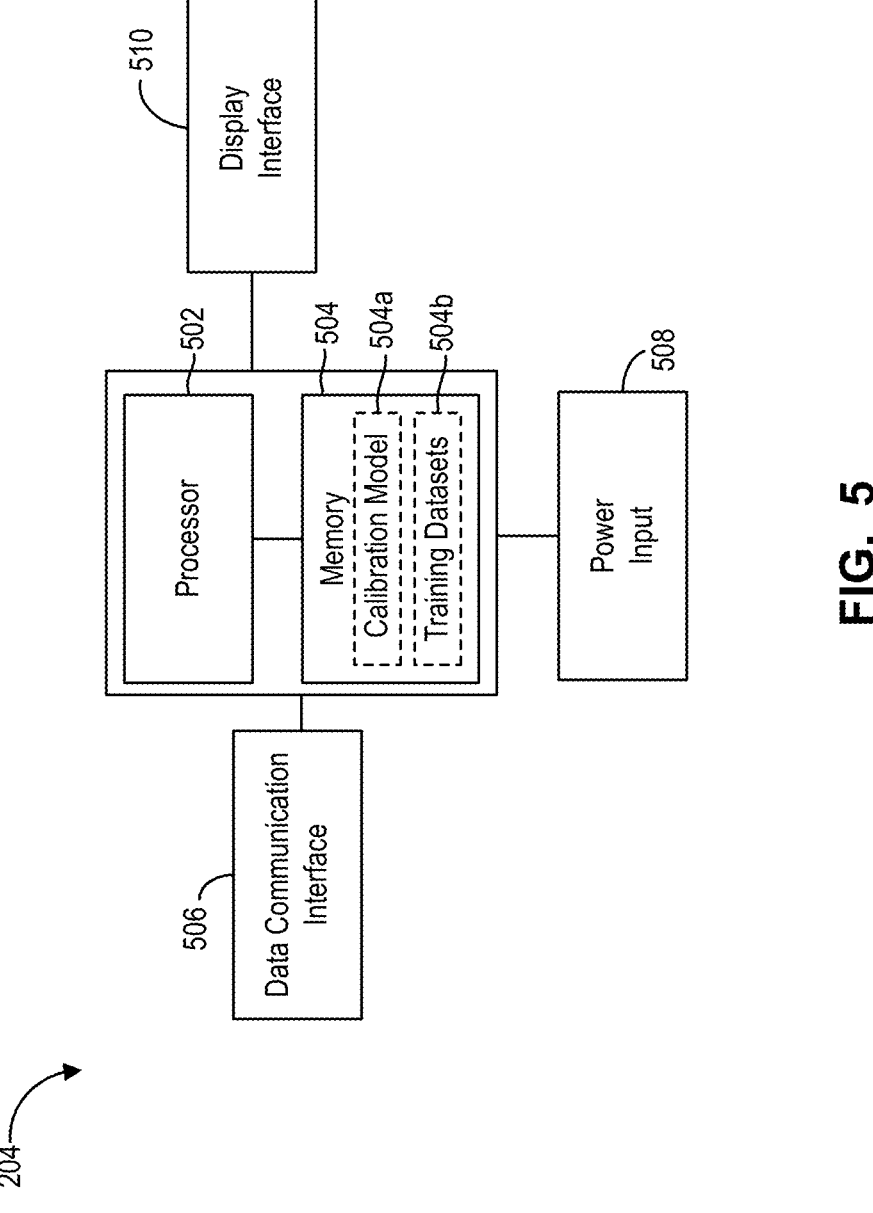
FIG. 5 is a simplified hardware/software block diagram of an example computer server.

Considering first the training of the calibration model (650*a*)—at act (602*b*), the calibration model is trained using one or more generated training dataset points, e.g., training datasets (504*b*) (FIG. 5). The training datasets can comprise a data structure including one or more points generated via any number of iterations of method (600*a*).

In this example, a simplified case is assumed whereby all training dataset points relate to the same AP (e.g., CO concentration). That is, acts (602*b*)-(606*b*) are regarded as exemplifying the training of a single AP-specific calibration model. However, acts (602*b*)-(606*b*) can also be used to separately train any number of AP-specific calibration models, using any number of relevant training datasets.

In at least one example, the calibration model (504*a*)—which is trained at (650*a*)—is a machine learning model. Further, the training algorithm may implement machine learning techniques, known to persons skilled in the art of artificial intelligence.

As non-limiting examples, the machine learning model may have an architecture in the form of an artificial neural network (ANN), a regression model including a linear and/or non-linear regression model, decision-tree model, support-vector machine classification models, or Bayesian or belief network model, among others.

Training algorithms are known to persons skilled in the art of machine learning. The selection of a training algorithm that is suitable for a particular machine learning model is within the skill of persons of ordinary skill in the art. In embodiments, the machine learning model and training algorithms may be implemented using available software environments or platforms, with non-limiting examples including Google Colaboratory™ (also known as Colab™) (Google Research), Juptyer™ (also known as IPython™) (Project Jupyter), and Anaconda™ (Anaconda, Inc.; Austin, TX, USA).

With continued reference to FIG.. 6B, at act (604*b*), a determination is made as to whether the calibration model is trained. In some examples, the calibration model is trained once a loss function (e(k)), in Equations (2) or (3)—described further below—is determined to be below a predetermined threshold.

If the calibration model is not trained, then the method (600*b*) can return to act (602*b*), to continue training the model. For example, the model can be trained using new, or additional training dataset points.

To that end, the present disclosure is not limited by the number of training dataset points used for training of the calibration model, which may depend on factors such as the type of measured APs, and a particular sample of the training values. As an example, tens of thousands of training values may be used for training of an AP-specific calibration model.

Otherwise, at act (606*b*), the trained calibration model is output. In some examples, the trained calibration model is stored on memory (504) of the server computer (204) for "offline" use. In other examples, the trained calibration model is transmitted to external computing systems. For example, the trained calibration model is transmitted, stored and hosted directly on any data acquisition system (106). In this manner, the trained calibration model is directly accessible by a data acquisition system (106). The model can also be stored and hosted on any number of reference units (202).

As noted previously, acts (602*b*)-(606*b*) can iterate to separately generate one or more AP-specific machine learning models. By generating AP-specific models, the models are more specifically trained to calibrate an associated AP, thereby generating more accurate results for that AP.

Continuing with reference to FIG. 6B, at a subsequent point in time, the trained AP-specific model is applied to newly measured AP values by the data acquisition system (DAS) (106). This can be the same DAS (106) used for training, or otherwise, any other DAS (106).

For example, at act (608*b*) the trained calibration model can receive an input AP value generated by a sensor of the DAS (106).

For example, in FIG. 1, the data acquisition system (DAS) (106) can generate new sensor data as it navigates again along the data collection route (104). The generated sensor data can measure an AP value at a point along the same route (104), or any other route. Accordingly, this new sensor data is received by the system at act (608*b*). In other examples (FIG. 3D), new sensor data is generated by a stationary DAS (106).

At act (610*b*), in some examples, one or more time-paired accuracy enhancing parameters can also be received. The accuracy enhancing parameters can be generated in analogous manner as act (610*a*), in FIG. 6A, and at the same time instance as the newly measured AP value is generated.

In examples where the trained calibration model is hosted on the server (204)—the received un-calibrated AP value (608*b*) from DAS (106), as well as the accuracy enhancing parameters (612*b*), are received at server (204), via network (306). For example, the data acquisition system (DAS) (106) can transmit the values and parameters to the server (204), via network (206).

At act (612b), the trained calibration model is applied to the input values comprising: (i) the measured un-calibrated AP value (608b), and (ii) in some examples, the one or more time-paired accuracy enhancing parameters.

In cases where the memory stores multiple AP-specific models, act (612b) can further involve, initially, selecting the correct AP-specific model to apply to the input values. For example, if the un-calibrated ambient AP is "CO" gas (act (608b)), then the system can identify the correct trained AP-specific model associated with CO gas, and apply that model.

To that end, each AP-specific model can be stored in server memory with an associated label, identifying the AP associated with that model. This, in turn, can facilitate the selection process at act (612b).

At act (614b), the calibration model generates an esti-mated calibrated ambient AP value. In other words, the calibration model adjusts for calibration offsets in sensor data, measured by the data acquisition system (DAS) (106).

In at least one example, the calibrated AP value (614b) is output on a display interface (510) of the server (204). In other example, the calibrated AP value (614b) is stored on a memory (504) of the server (204), or a memory (404) of the DAS (106), or a memory of the cloud database (208). The stored calibrated value can be accessed immediately, or at a future point in time for further data analysis and processing.

In at least one embodiment, acts (608b)-(614b) are per-formed in real-time, or near real-time, such as to provide real-time calibration of AP values generated by the data acquisition system (106). That is, the elapsed time from the measurement of the input value of the un-calibrated AP, at act (608b), to the output at act (614b), is practically instan-taneous, being practically limited only by any latency in the communication and processing of the sensor data and out-put.

In some examples, acts (608b)-(614b) are performed "offline" (or otherwise, not in real-time or near real-time).

For example, the un-calibrated AP values, and accuracy-enhancing parameters, may have been previously obtained. Further, they may have been previously stored on a memory of the server (204), cloud database (208) and/or data acqui-sition system (106). In this example, the trained calibration model retrieves the previously acquired datasets, and gen-erates the calibrated output.

(iv.) Continuous Training of Calibration Model

In some examples, even after act (606b) is complete, the system can continue iterating the training, during model application (i.e., the inference phase). That is, the model can be continuously or frequently trained in the background (i.e., acts (602b)-(606b)), even while it's being applied. This allows continuously enhancing the predictive accuracy of the model (see e.g., return arrow from (612b) to (602b)).

In these examples, a new training dataset point is gener-ated based on: (i) the un-calibrated AP values from the data acquisition system (106), at (608b); (ii) a time-paired mea-sured AP from a target reference unit (608a); (iii) a positive scale factor (h(k)), and/or (iv) time-paired accuracy-enhanc-ing parameters (610a, 610b).

The training dataset point is generated using real-time or near real-time data and used to re-train the model, also in real-time or near real-time. This re-training can occur "offline" if the trained model is hosted directly on the data acquisition system (106).

IX. Example Machine Learning Model and Training

The following is a discussion of an example machine learning architecture and training algorithm, that can be used during method 600b (FIG. 6B).

(i.) Example Architecture for Machine Learning Model

Figure 8:
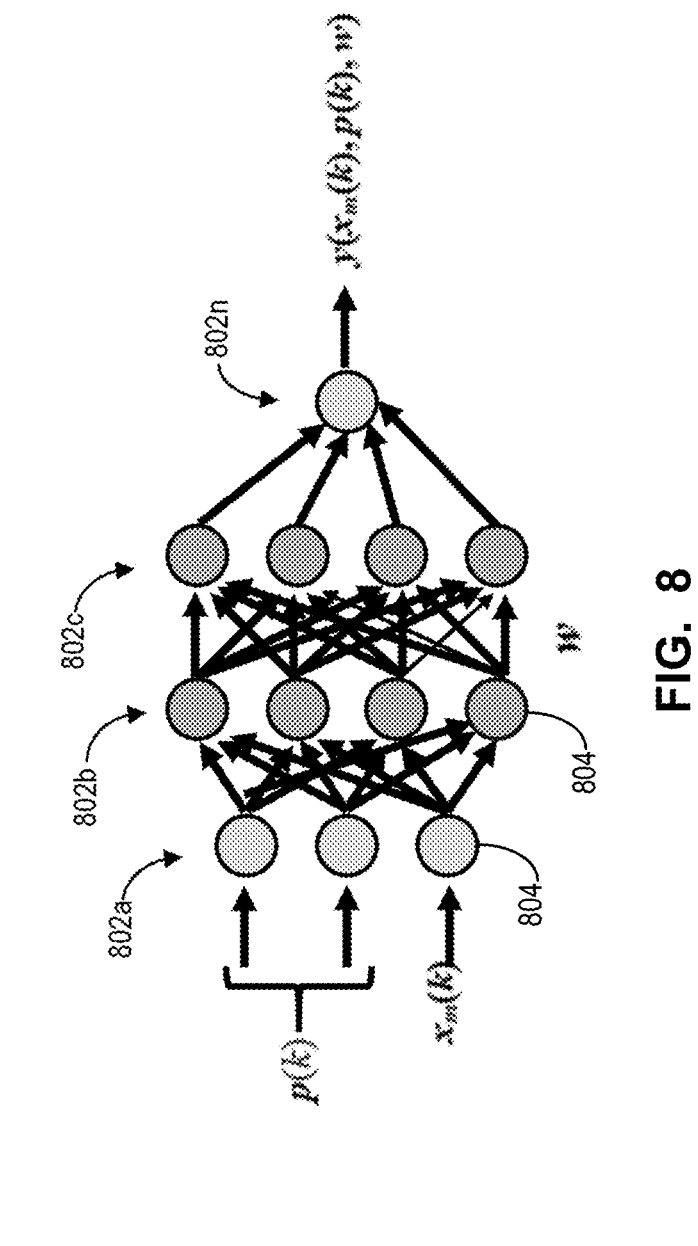
FIG. 8 is an example architecture for an artificial neural network (ANN).

FIG. 8 shows an example architecture for an ANN (800) that can be trained, to generate a trained AP-specific cali-bration model.

The ANN (800) is trained by receiving input features, corresponding to: (i) the measured un-calibrated ambient AP value from the mobile sensor ($X_m(k)$), (ii) in some example, the time-paired "accuracy-enhancing parameters" (p(k)); and/or (iii) scale factor (h(k)), and the output features corresponding to the calibrated measured AP value ($x_s(k)$).

The ANN (800) includes a number of "layers" (802a)-(802n), wherein each layer includes one or more neuron nodes (804). Each node (804) has an assigned node weight, such that the aggregate of the node weights is represented by the weight matrix (w).

In at least one example, the ANN (800) is composed of three layers (802a), (802b) and (802c), each comprising three hidden neuron nodes (804).

The training can occur using a stochastic gradient descent technique. In one example, an Adam (Adaptive Moment Estimation) optimization algorithm, for deep learning mod-els, is used. Adam optimization is a stochastic gradient descent method that is based on adaptive estimation of first-order and second-order moments, as is known in the art.

An Adam optimization is known to be "computationally efficient, has little memory requirement, invariant to diago-nal rescaling of gradients, and is well suited for problems that are large in terms of data/parameters" (see e.g., Diederik P. Kingma, Jimma Ba "Adam: A Method for Stochastic Optimization", ICLR 2015). Accordingly, the use of an Adam optimization algorithm is suited for small factor, low processing power applications (i.e., training on the data acquisition system). In other examples, any other Adam variant can be used, e.g., Nadam (Nesterov-accelerated Adaptive Moment Estimation), AdaMax, AMSGrad, etc.

In at least one example, the training was performed using Keras® software. The ANN inputs and outputs were scaled (i.e., mapped) to a value between 0 and 1 using a MinMax scaler to optimize training time and efficiency, i.e., and accommodate low-processing applications. In some examples, the default hyper parameters were used applying the Adam optimization algorithm using the Keras® soft-ware, namely:

Learning Rate: 0.001;

Beta 1: 0.9;

Beta 2: 0.999;

Epsilon: 1e-7; and

Amsgrad: False.

In one example, the training dataset file included 30 samples, and the number of iterations to train the model was 1,000 iterations.

Figure 9:
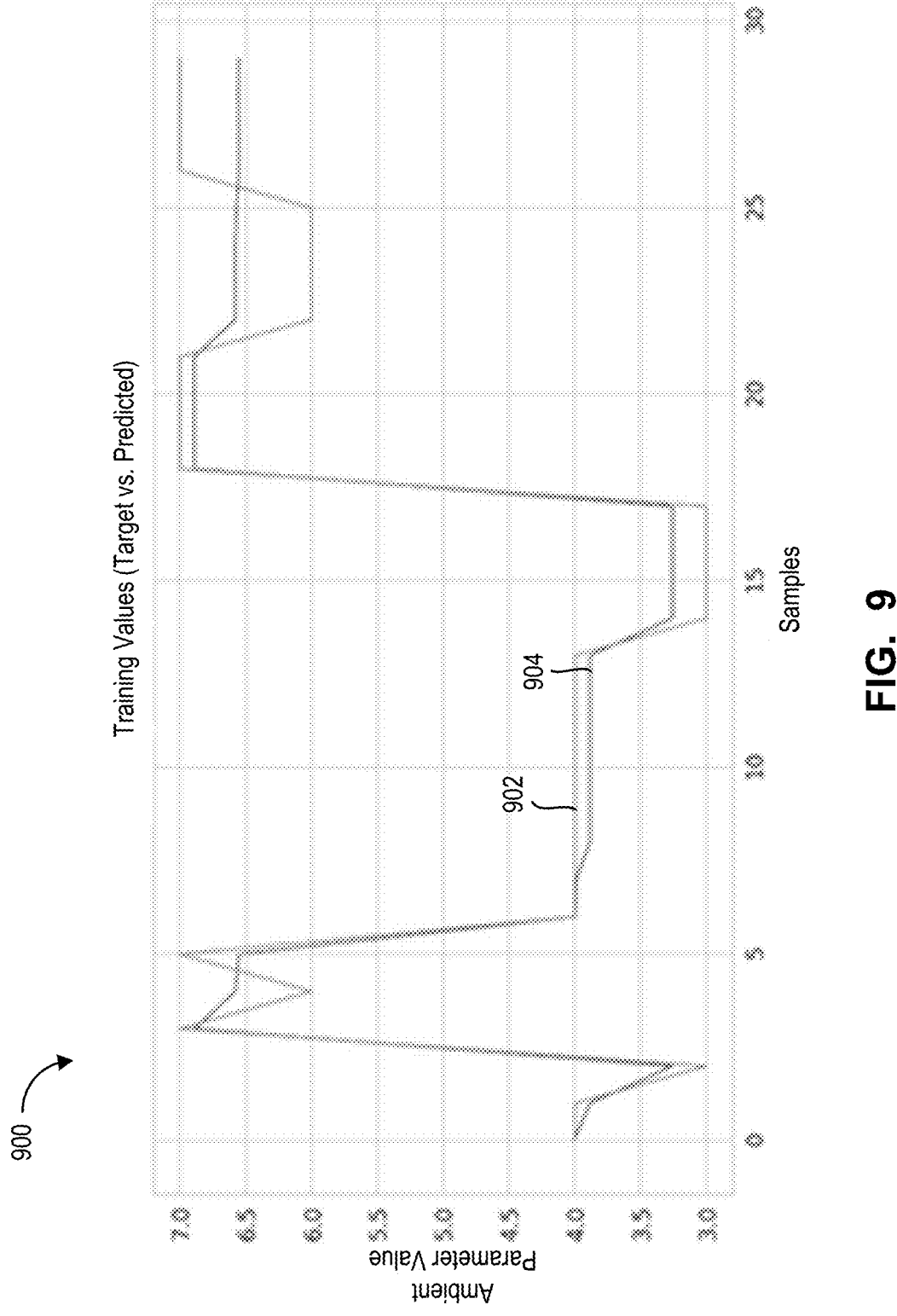
FIG. 9 is a plot of expected versus predicted values for a monitored ambient parameter.

FIG. 9 shows a plot (900) for an example output of a trained AP-specific calibration model, whereby the plot line (902) is the AP value measured by an accurate stationary reference unit, and the plot line (904) is the AP value predicted using a trained calibration model. As shown, the two plot lines closely follow each other, thereby demonstrating the efficacy of the trained model.

(ii.) Example Loss Function

As stated in method (600b), in some examples, the objective is to train the calibration model with a view to minimizing a loss function. If the loss function is below a pre-determined value, the model is assumed to be sufficiently trained (606b).

More generally, the training algorithm adjusts parameters of the calibration model to minimize the value of a loss function, which is when the calibration model is considered to be "trained".

In some examples, the objective of training the calibration model is to minimize an objective function $f(w)$. The objective function $f(w)$ represents the difference between the output of the ANN, $y(x(k), p(k), w)$, and the desired output $\tilde{x}(k)$, where w is the vector of weights of the ANN, wherein: (i) x(k) is a measured un-caliberated AP by the data acquisition system (106); (ii) p(k) is a vector of accuracy-enhancing parameters; (iii) w is a vector of the weights of the ANN nodes; and (iv) $\tilde{x}(k)$ is a measured AP from a reference sensor (202).

In more detail, the desired output x(k) is expressed by the measured AP value $X_s(k)$ by the relevant reference unit (202) at the k-th time step (614a in FIG. 6A). The objective function is minimized when the ANN generates an estimated calibrated output, for the AP value—measured by the data acquisition system (DAS) sensor—that is substantially similar to the target AP value, measured by the stationary unit (202), at the k-th time step, i.e., $x_s[k]$.

Among the parameters that are adjusted by minimizing the objective function $f(w)$ are the number of "layers" that make up the ANN, and the number of "neurons" or "nodes" within each layer. These parameters may be pre-assigned by an operator prior to training the ANN, and then adjusted through an iterative process.

The output of the ANN is an estimated calibrated AP value (y), which is a function of: (i) the un-calibrated measured AP value from the data acquisition system sensor, (ii) the accuracy-enhancing parameters, and (iii) the weight matrix (i.e., $y(x_m(k), p(k),w)$).

The training optimization problem can be expressed by Equation (1):

$$w^*=\arg \min f(w) \qquad (1)$$

where the objective function aims at optimizing the weights (w*) to achieve the least possible value of all the errors e(k) as expressed by Equation (2):

$$e(k) = |y(x(k), p(k), w) - \tilde{x}(k)|, k \in K \qquad (2)$$

where K is the set of time indexes corresponding to the time instance (also referenced as "thin time slices") over which the data acquisition system (106) passes in the proximity of the accurate reference units (202) and generates a training dataset point.

In some examples, the error function e(k) is also expressed in accordance with Equation (3):

$$e(k) = h(k)|y(x(k), p(k), w) - \tilde{x}(k)|, k \in K \qquad (3)$$

wherein h(k) is the positive scale factor determined for the k-th time step (614a in FIG. 6A), and that puts more emphasis on the minimizing the errors corresponding to the time instances when the data acquisition system (106) is closest to the reference units (202) (FIG. 7).

X. Small Form Factor

The data acquisition system (DAS) (106) may be encapsulated in a small form factor, light weight enclosure. In some examples, the DAS (106) is encapsulated in a 2.2"× 6"×6" enclosure that weights approximately 2 lbs. or less.

The small, lightweight enclosure is easily mounted to various fixed or mobile platforms (102) (e.g., without specialized deployment skills required). In this manner, the system (200) is highly-scalable, and can include any number of data acquisition systems (106) mounted to fixed poles, or a fleet of vehicles (102). In turn, this allows for ambient parameter (AP) monitoring across a wider geographic area.

As stated earlier, encapsulating the data acquisition system (106) in a small form factor, lightweight enclosure is enabled by relying on data processing for calibration. This is contrasted to systems which rely on large and expensive hardware calibrators and/or stabilizers for high-end sensors (e.g., temperature and humidity stabilizers or vibration platforms), and which are not scalable in the same manner

XI. Alternative and Specific Embodiments

While method (600a) exemplifies a simplified case for generating training dataset points for a single AP type (e.g., CO concentrations values), method (600a) can be used for generating training dataset points for any number of AP types. This can enable the training values to be used for generating for training any number of AP-specific calibration models.

Further, in the embodiments of the method (600a) and (600b) described above, it is assumed that the method is implemented by server processor (502) executing instructions stored on server memory (504) of server computer (204). In other embodiments, any one or more of these act may be implemented by data acquisition system processor (402) executing instructions stored on memory (404) local to the data acquisition system (106). In such embodiments, the processing of these steps may be performed "offline" (without a need for a communications network to transmit the data to another computer system), and the results of methods (600a) and (600b) may be stored in the memory (404) or another memory local to the data acquisition system (106) for retrieval or downloading at a later time.

In still other embodiments, the instructions executed by either or both of the processors (402, 504) may be stored entirely either on memory (404) or memory (504), or in a combination of memories (404, 504). Accordingly, in embodiments, any one or more of these acts, or further computational acts may be implemented entirely by processor (402) of data acquisition system (106), entirely by processor (502) of server (204), or by a combination of the processors (402, 502) executing instructions stored entirely either on memory (404) of data acquisition system (106) or on memory (504) of server computer (204), or on a combination of memories (404, 504). Any combination of processor(s) and memory or memories implementing these steps may be considered as the "computer system" in the method shown in FIGS. 6A-6B, and other methods described herein.

In some examples, in method (600a)—act (612a) can provide an alternative to acts (602a) and (604a). That is, where the positive scale factor is determined, at act (612a), it may not be necessary to initially determine that the data acquisition system (106) is within proximity of a reference sensor units (202) as a "condition" to generating a training dataset point. Rather, the scale factor (h(k)) can function as a logical mathematical filter, in Equation (3), for eliminating training dataset values generated outside the boundary region (302) (FIG. 3).

For example, in method (600a), rather than completing acts (602a) and (604a)-time-paired training dataset values are generated continuously by the system, or at the sensor sampling rate. Training values that are generated outside the boundary region (302) (FIG. 6) are automatically assigned a positive scale factor of "0". Accordingly, during calibration model training, these training values are weighted by a zero factor, thereby automatically negating the relevance of these values in Equation (3). In this manner, the positive scale factors function to filter training dataset values obtained far away from the reference unit (202), without performing acts (602a) and (604a).

In methods (600a) and (600b), where a reference unit (202) is equipped with one or more types of sensors, the reference unit (202) can transmit different sensor readings, wherein each sensor reading is labelled with the AP associated with that sensor readings. In this manner, the system is able to distinguish between different types of received sensor data.

In some cases, the system may have pre-defined knowledge of which types of sensors are equipped by each reference unit (202). Accordingly, upon receiving sensor data from that unit, the system can automatically determine the type of AP associated with that sensor reading.

XII. Example Hardware Configurations

Various example hardware configurations for various systems and devices are now described herein.

(i.) Example Configuration for Data Acquisition System

Figure 4:
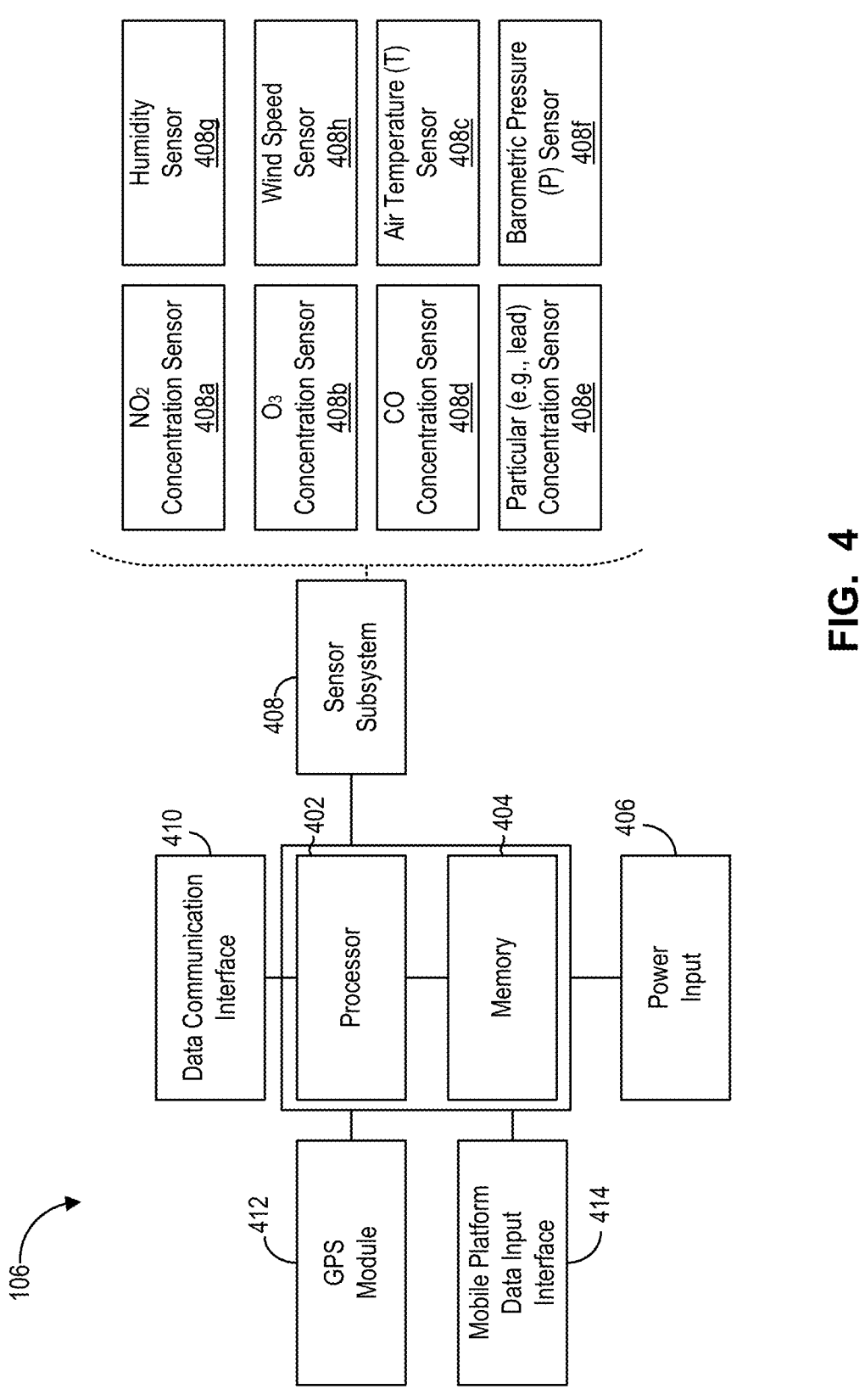
FIG. 4 is a simplified hardware/software block diagram of an example data acquisition system.

Reference is now made to FIG. 4, which shows a simplified block diagram for an example hardware architecture for a data acquisition system (106).

As shown, the data acquisition system (106) can include at least one processor (402) operatively coupled, via a computer data bus, to one or more of a memory (404), a power input (406), a sensor subsystem (408), a data communication interface (410), a GPS module (312). In some examples, the processor (402) is also coupled to a mobile platform data input interface (314).

Sensor subsystem (408)—also referenced herein as a data acquisition system (DAS) sensor subsystem (408)—can include one or more DAS sensors (408a)-(408h).

In at least one example, the sensor subsystem (408) can include sensors which measure various ambient parameters (APs), including various ambient gas parameters.

Examples of sensors in the sensor subsystem (408) for measuring ambient gas parameters include a nitrogen dioxide concentration sensor (408a), an ozone concentration sensor (408b), a carbon monoxide concentration sensor (408d) and a particular concentration (e.g., lead concentration) sensor (408e).

Sensor subsystem (408) can also include a number of other sensors, for measuring other ambient parameters. By way of example, these include a relative humidity (RH) sensor (408g), a wind speed sensor (408h), an air temperature (T) sensor (408c) and a barometric pressure (P) sensor (408f).

More generally, sensor subsystem (408) may be implemented by digital electrochemical sensors, thermometers, pressure sensors, hygrometers, anemometers, and other sensor devices known in the art that are capable of measuring the applicable APs of interest to generate sensor data in digital form.

In at least one example, sensors—comprising sensor subsystem (408)—are physically proximate to each other. In this manner, the sensors generate sensor data (e.g., air quality) in substantially the same location. The sensors, or sensor subsystem (408), may be attached to a common housing mounted on a mobile platform (102), such as vehicle (102).

Processor (402) and memory (404) can collectively form a microcontroller. The microcontroller includes firmware coded in memory (404) configuring processor (402) to control sensor subsystem (408) for acquisition of sensor data, and to control data communication interface (410) for transmission of sensor data via a communications network. It will be understood by those of skill in the art that references herein to data acquisition system (106) as carrying out a function or acting in a particular way imply that processor (402) is executing instructions (e.g., a software program) stored in memory (404) and possibly transmitting or receiving inputs and outputs via one or more interface.

Power input (406) may receive electrical power from a supply such as a battery of the mobile system (106), or a vehicle or other type of mobile platform, or a solar panel.

Data communication interface (410) may comprise any combination of hardware and/or software that allows for transmission of the sensor data from mobile system (106) via a communications network (206). In at least one embodiment, data communication interface (410) may comprise a cellular modem and antenna for wireless transmission of sensor data to the communications network.

GPS module (412) generates location data, indicative of the location of the data acquisition system (106). In some cases, GPS module (412) generates other kinematic data of the data acquisition system (106), such as its distance travelled, direction of movement, speed, and/or acceleration.

Mobile platform data input interface (414) may comprise any combination of hardware and software for receiving data from a system of a mobile platform (102) to which a mobile data acquisition system (106) may be mounted.

For example, in embodiments where the mobile platform (102) is a vehicle or a portable computer equipped with its own GPS module and/or telematics system for monitoring the mobile platform's location, distance travelled, direction of movement, speed, and/or acceleration—the mobile platform data input interface (414) may comprise a wired or wireless data bus for communication with such GPS module and/or telematics system. Thus, the data acquisition system (106) may "piggyback" on the mobile platform's GPS module and/or telematics system, and the data acquit ion system (106) need not have its own GPS module (412). Data received from the mobile platform data input interface (414) is referenced herein collectively as mobile platform data.

While not explicitly illustrated, the data acquisition system (106) can also include an analog-to-digital converter (ADC), interposed between and otherwise coupling the processor (402) to the sensor subsystem (408). The ADC can be a high resolution ADC to maintain highly accurate digital conversion of sensor readings. For example, the ADC may have 16-bit or 24-bit resolution. In various examples, sensor data processed by the ADC is used during training of the calibration model(s).

(ii.) Example Configuration for Reference Sensor Unit

While not explicitly shown, each reference sensor unit (202) may have an analogous architecture to the data acquisition system (106). In other words, the reference units (202) may also have a corresponding processor coupled to a memory, a reference unit sensor subsystem and a data communication interface. The sensor subsystem can include one or more sensors for monitoring various types of APs in a localized area, around the reference units (202), as well as high resolution ADC. The sensor units (202) may not, however, necessarily always include a GPS module (412) or a mobile platform data input interface (414). However, these can be included if the reference unit is mobile.

As noted previously, a differentiating factor is that the sensor subsystem—in the reference sensor units (202)—may use higher quality, more expensive sensors (e.g., scientific-grade sensors). Further, the reference sensor units (202) can also include other hardware (e.g., calibration or stabilization hardware), as explained previously.

In at least one example, multiple reference units (202) may share some common hardware. For example, multiple reference units (202) may share a common processor, memory and/or communication interface. In some example, different reference sensor units (202) may have sensor subsystems (408) equipped with different types of sensors, for measuring different types of APs.

(iii.) Example Hardware Configuration for Computer Server

Reference is now made to FIG. 5, which shows a simplified block diagram of an example computer server (304).

As shown, the computer server (304) includes a processor (502) operatively connected to one or more of a memory (504), a power input (508), a data communication interface (506), and optionally a display device (510).

In at least one embodiment, processor (502) may be implemented by a CPU, and memory (504) may be implemented by a hard drive or solid-state memory. It will be understood by those of skill in the art that references herein to server (204) as carrying out a function or acting in a particular way imply that processor (502) is executing instructions (e.g., a software program) stored in memory (504) and possibly transmitting or receiving inputs and outputs via one or more interface.

In some examples, memory (504) stores a trained calibration model (504a) trained to calibrate AP values generated by one or more mobile sensors. The instructions, corresponding to the trained model, are executable by processor (502) to implement steps of the method of the present disclosure as described below.

Memory (504) can also store training dataset values (504b), which are used to train an initially un-trained calibration model, which can also be hosted on memory (504). As explained herein, the training dataset values (504b) can correspond to an aggregate of AP values generated by mobile and stationary sensors, among other sensors.

Data communication interface (506) may comprise any combination of hardware and/or software that allows for reception of sensor data, and transmission of output data via a communications network. In some embodiments, data communication interface (506) may comprise an Internet modem.

Display device (510) may be any device that allows for display of data in text and/or graphical form. In some embodiments, the display device (510) is a computer display monitor.

XIII. Interpretation

Aspects of the present invention may be described with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The corresponding structures, materials, acts, and equivalents of all means or steps plus function elements in the claims appended to this specification are intended to include any structure, material, or act for performing the function in combination with other claimed elements as specifically claimed.

References in the specification to "one embodiment", "an embodiment", etc., indicate that the embodiment described may include a particular aspect, feature, structure, or characteristic, but not every embodiment necessarily includes that aspect, feature, structure, or characteristic. Moreover, such phrases may, but do not necessarily, refer to the same embodiment referred to in other portions of the specification. Further, when a particular aspect, feature, structure, or characteristic is described in connection with an embodiment, it is within the knowledge of one skilled in the art to affect or connect such module, aspect, feature, structure, or characteristic with other embodiments, whether or not explicitly described. In other words, any module, element or feature may be combined with any other element or feature in different embodiments, unless there is an obvious or inherent incompatibility, or it is specifically excluded.

It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation. The terms "preferably," "preferred," "prefer," "optionally," "may," and similar terms are used to indicate that an item, condition or step being referred to is an optional (not required) feature of the invention.

The singular forms "a," "an," and "the" include the plural reference unless the context clearly dictates otherwise. The term "and/or" means any one of the items, any combination of the items, or all of the items with which this term is associated. The phrase "one or more" is readily understood by one of skill in the art, particularly when read in context of its usage.

The term "about" can refer to a variation of +5%, +10%, +20%, or +25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values and ranges proximate to the recited range that are equivalent in terms of the functionality of the composition, or the embodiment.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc.

As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio.

The invention claimed is:

1. A method performed by a vehicle mounted data acquisition system (DAS) comprising:

measuring, by at least one gaseous component concentration sensor comprised by the vehicle mounted DAS, a concentration of gas;

receiving, by an analog to digital converter connected to a processor, an analog signal from the gaseous component concentration sensor that represents the measured concentration of gas;

generating, by the analog to digital converter, an uncalibrated sensor value $x_m(k)$ that indicates the measured concentration of gas, wherein k is an integer time index;

measuring a speed of the vehicle mounted DAS that is time-paired with the uncalibrated sensor value $x_m(k)$ and include the speed of the vehicle mounted DAS in a vector of accuracy enhancing parameters $p(k)$;

receiving, from a cloud server, reference unit location information indicating a location of a geographically fixed reference unit that is external to the vehicle mounted DAS, wherein the geographically fixed reference unit comprises at least one gaseous component concentration sensor and hardware that stabilizes vibration of the at least one gaseous component concentration sensor;

determining a distance from the vehicle mounted DAS to the geographically fixed reference unit based on the received reference unit location information;

determining whether or not the distance from the vehicle mounted DAS to the geographically fixed reference unit is less than a threshold distance;

in circumstances where the distance from the vehicle mounted DAS to the geographically fixed reference unit is less than a threshold distance:

receive a reference sensor value $x_s(k)$ from the geographically fixed reference unit, wherein the reference sensor value $x_s(k)$ corresponds with at least one measurement of the at least one gaseous component concentration sensor comprised by the geographically fixed reference unit that is time-paired with the uncalibrated sensor value $x_m(k)$;

calculate a trust weight $h(k)$ that is time-paired with the uncalibrated sensor value $x_m(k)$ such that the trust weight $h(k)$:

is inversely proportional to the speed of the vehicle mounted DAS, and is inversely proportional to the distance from the vehicle mounted DAS to the geographically fixed reference unit;

generate a training dataset point according to $([x_m(k)p(k)^T], x_s(k)], h(k))$;

training a calibration model using the training dataset point;

applying the calibration model to the uncalibrated sensor value $x_m(k)$ and the vector of accuracy enhancing parameters $p(k)$ to generate a calibrated sensor value; and wirelessly transmitting the calibrated sensor value to the cloud server;

in circumstances where the distance from the vehicle mounted DAS to the geographically fixed reference unit is not less than a threshold distance:

applying the calibration model to the uncalibrated sensor value $x_m(k)$ and the vector of accuracy enhancing parameters $p(k)$ to generate a calibrated sensor value; and wirelessly transmitting the calibrated sensor value to the cloud server.

2. The method of claim 1, wherein the at least one gaseous component concentration sensor comprised by the vehicle mounted DAS is at least one non-scientific grade sensor and the at least one gaseous component concentration sensor comprised by the geographically fixed reference unit is at least one scientific grade sensor.

3. The method of claim 1, wherein the determining a distance from the vehicle mounted DAS to the geographically fixed reference unit based on the received reference unit location information comprises:

receiving, by the processor, from a GPS module connected to the processor, a signal indicating the geographical location of the vehicle mounted DAS; and calculating, by the processor, a distance between the geographical location of the vehicle mounted DAS and the received reference unit location.

4. The method of claim 1, wherein the gaseous component concentration sensor is configured to measure the concentration of gas in air, and the gas is at least one of carbon monoxide (CO), carbon dioxide ($CO_2$), nitrous oxide (NO), nitrogen dioxide ($NO_2$), ozone ($O_3$), methane ($CH_4$), or sulfur dioxide ($SO_2$).

5. The method of claim 1, wherein the trained calibration model is a trained machine learning model.

6. The method of claim 5 wherein the calibration model is a trained artificial neural network (ANN).

7. A vehicle mounted data acquisition system (DAS) comprising:

a processor;

an analog to digital converter connected to the processor;

at least one gaseous component concentration sensor connected to the analog to digital converter;

memory connected to the processor, wherein the memory comprises instructions that, when read by the processor, cause the processor to:

measure, by the at least one gaseous component concentration sensor, a concentration of gas;

receive, via the analog to digital converter connected to a processor, an analog signal from the gaseous component concentration sensor that represents the measured concentration of gas;

generate, by the analog to digital converter, an uncalibrated sensor value $x_m(k)$ that indicates the measured concentration of gas, wherein k is an integer time index;

measure a speed of the vehicle mounted DAS that is time-paired with the uncalibrated sensor value $x_m(k)$ and include the speed of the vehicle mounted DAS in a vector of accuracy enhancing parameters p(k);

receive, from a cloud server, reference unit location information indicating a location of a geographically fixed reference unit that is external to the vehicle mounted DAS, wherein the geographically fixed reference unit comprises at least one gaseous component concentration sensor and hardware that stabilizes vibration of the at least one gaseous component concentration sensor;

determine a distance from the vehicle mounted DAS to the geographically fixed reference unit based on the received reference unit location information;

determine whether or not the distance from the vehicle mounted DAS to the geographically fixed reference unit is less than a threshold distance;

in circumstances where the distance from the vehicle mounted DAS to the geographically fixed reference unit is less than a threshold distance:

receive a reference sensor value $x_s(k)$ from the geographically fixed reference unit, wherein the reference sensor value $x_s(k)$ corresponds with at least one measurement of the at least one gaseous component concentration sensor comprised by the geographically fixed reference unit that is time-paired with the uncalibrated sensor value $x_m(k)$;

calculate a trust weight h(k) that is time-paired with the uncalibrated sensor value $x_m(k)$ such that the trust weight h(k):

is inversely proportional to the speed of the vehicle mounted DAS, and is inversely proportional to the distance from the vehicle mounted DAS to the geographically fixed reference unit;

generate a training dataset point according to ($[x_m(k)p(k)^T], x_s(k)]$, h(k));

train a calibration model using the training dataset point;

apply the calibration model to the uncalibrated sensor value $x_m(k)$ and the vector of accuracy enhancing parameters p(k) to generate a calibrated sensor value; and wirelessly transmit the calibrated sensor value to the cloud server;

in circumstances where the distance from the vehicle mounted DAS to the geographically fixed reference unit is not less than a threshold distance:

apply the calibration model to the uncalibrated sensor value $x_m(k)$ and the vector of accuracy enhancing parameters p(k) to generate a calibrated sensor value; and wirelessly transmit the calibrated sensor value to the cloud server.

8. The vehicle mounted DAS of claim 7, wherein the at least one gaseous component concentration sensor comprised by the vehicle mounted DAS is at least one non-scientific grade sensor and the at least one gaseous component concentration sensor comprised by the geographically fixed reference unit is at least one scientific grade sensor.

9. The vehicle mounted DAS of claim 7, wherein when the processor is caused to determine a distance from the vehicle mounted DAS to the geographically fixed reference unit based on the received reference unit location information, the determination comprises that the processor is further caused to:

receive, from a GPS module connected to the processor, a signal indicating the geographical location of the vehicle mounted DAS; and calculate a distance between the geographical location of the vehicle mounted DAS and the received reference unit location.

10. The vehicle mounted DAS of claim 7, wherein the gaseous component concentration sensor comprised by the vehicle mounted DAS is configured to measure the concentration of gas in air, and the gas is at least one of carbon monoxide (CO), carbon dioxide ($CO_2$), nitrous oxide (NO), nitrogen dioxide ($NO_2$), ozone ($O_3$), methane ($CH_4$), or sulfur dioxide ($SO_2$).

11. The vehicle mounted DAS of claim 7, wherein the trained calibration model is a trained machine learning model.

12. The vehicle mounted DAS of claim 11 wherein the calibration model is a trained artificial neural network (ANN).

13. A non-transitory computer readable medium that includes instructions that, when read by a processor of a vehicle mounted data acquisition system (DAS), cause the processor to:

cause measurement, by at least one gaseous component concentration sensor comprised by the vehicle mounted DAS, a concentration of gas;

receive, via an analog to digital converter connected to a processor, an analog signal from the gaseous component concentration sensor comprised by the vehicle mounted DAS that represents the measured concentration of gas;

generate, by the analog to digital converter, an uncalibrated sensor value $x_m(k)$ that indicates the measured concentration of gas, wherein k is an integer time index;

measure a speed of the vehicle mounted DAS that is time-paired with the uncalibrated sensor value $x_m(k)$ and include the speed of the vehicle mounted DAS in a vector of accuracy enhancing parameters p(k);

receive, from a cloud server, reference unit location information indicating a location of a geographically fixed reference unit that is external to the vehicle mounted DAS, wherein the geographically fixed reference unit comprises at least one gaseous component concentration sensor and hardware that stabilizes vibration of the at least one gaseous component concentration sensor;

determine a distance from the vehicle mounted DAS to a geographically fixed reference unit based on the received reference unit location information;

determine whether or not the distance from the vehicle mounted DAS to the geographically fixed reference unit is less than a threshold distance;

in circumstances where the distance from the vehicle mounted DAS to the geographically fixed reference unit is less than a threshold distance:

receive a reference sensor value $x_s(k)$ from the geographically fixed reference unit, wherein the reference sensor value $x_s(k)$ corresponds with at least one measurement of the at least one gaseous component concentration sensor comprised by the geographically fixed reference unit that is time-paired with the uncalibrated sensor value $x_m(k)$;

calculate a trust weight h(k) that is time-paired with the uncalibrated sensor value $x_m(k)$ such that the trust weight h(k):

is inversely proportional to the speed of the vehicle mounted DAS, and is inversely proportional to the distance from the vehicle mounted DAS to the geographically fixed reference unit;

generate a training dataset point according to ($[x_m(k)p(k)^T],x_s(k)]$, h(k));

train a calibration model using the training dataset point;

apply the calibration model to the uncalibrated sensor value $x_m(k)$ and the vector of accuracy enhancing parameters p(k) to generate a calibrated sensor value; and wirelessly transmit the calibrated sensor value to a cloud server;

in circumstances where the distance from the vehicle mounted DAS to the geographically fixed reference unit is not less than a threshold distance:

apply the calibration model to the uncalibrated sensor value $x_m(k)$ and the vector of accuracy enhancing parameters p(k) to generate a calibrated sensor value; and wirelessly transmit the calibrated sensor value to a cloud server.

14. The non-transitory computer readable medium of claim 13, wherein the at least one gaseous component concentration sensor comprised by the vehicle mounted DAS is at least one non-scientific grade sensor and the at least one gaseous component concentration sensor comprised by the geographically fixed reference unit is at least one scientific grade sensor.

15. The non-transitory computer readable medium of claim 13, wherein when the processor is caused to determine a distance from the vehicle mounted DAS to a geographically fixed reference unit based on the received reference unit location information the determination comprises that the processor is further caused to:

receive, from a GPS module connected to the processor, a signal indicating the geographical location of the vehicle mounted DAS; and calculate a distance between the geographical location of the vehicle mounted DAS and the received reference unit location.

16. The non-transitory computer readable medium of claim 13, wherein the gaseous component concentration sensor is configured to measure the concentration of gas in air, and the gas is at least one of carbon monoxide (CO), carbon dioxide ($CO_2$), nitrous oxide (NO), nitrogen dioxide ($NO_2$), ozone ($O_3$), methane ($CH_4$), or sulfur dioxide ($SO_2$).

17. The non-transitory computer readable medium of claim 13, wherein the trained calibration model is a trained machine learning model.

18. The non-transitory computer readable medium of claim 17 wherein the calibration model is a trained artificial neural network (ANN).

* * * * *